United States Patent
Levin et al.

(10) Patent No.: US 11,728,008 B2
(45) Date of Patent: Aug. 15, 2023

(54) MACHINE LEARNING AND CONTROL SYSTEMS AND METHODS FOR LEARNING AND STEERING EVOLUTIONARY DYNAMICS

(71) Applicant: Melonfrost, Inc., Brooklyn, NY (US)

(72) Inventors: Samuel R. Levin, Brooklyn, NY (US); Lucas J. Harrigan, Brooklyn, NY (US); Sean R. White, Brooklyn, NY (US); Loren K. Amdahl-Culleton, Brooklyn, NY (US)

(73) Assignee: Melonfrost, Inc., Brooklyn, NY (US)

( * ) Notice: Subject to any disclaimer, the term of this patent is extended or adjusted under 35 U.S.C. 154(b) by 0 days.

(21) Appl. No.: 17/465,291

(22) Filed: Sep. 2, 2021

(65) Prior Publication Data
US 2022/0068436 A1  Mar. 3, 2022

Related U.S. Application Data

(60) Provisional application No. 63/154,794, filed on Feb. 28, 2021, provisional application No. 63/074,132, filed on Sep. 3, 2020.

(51) Int. Cl.
*G16B 20/40* (2019.01)
*G16B 40/00* (2019.01)
(Continued)

(52) U.S. Cl.
CPC ............ *G16B 20/40* (2019.02); *C12M 41/12* (2013.01); *C12M 41/26* (2013.01); *C12M 41/34* (2013.01);
(Continued)

(58) Field of Classification Search
CPC ...... C12N 15/1058; G16B 20/40; G16B 5/20; G16B 40/00; C12M 41/12; C12M 41/26;
(Continued)

(56) References Cited

U.S. PATENT DOCUMENTS

2002/0025517 A1* 2/2002 Minshull ............ C12N 15/1027
435/6.18
2002/0127623 A1* 9/2002 Minshull .............. C12Q 1/6888
435/7.92
(Continued)

FOREIGN PATENT DOCUMENTS

WO  WO-2019/100040 A1  5/2019
WO  WO-2021067831 A1 *  4/2021  ......... C12N 15/1058

OTHER PUBLICATIONS

Lotfi, Khadije, et al. "Predicting wastewater treatment plant quality parameters using a novel hybrid linear-nonlinear methodology." Journal of environmental management 240 (2019): 463-474. (Year: 2019).*

(Continued)

*Primary Examiner* — Jesse P Frumkin
(74) *Attorney, Agent, or Firm* — Goodwin Procter LLP

(57) ABSTRACT

A technique for learning and steering evolutionary dynamics may include initializing a bioreactor including a population of evolving organisms; determining selection pressures; (a) applying the selection pressures to the population; (b) determining the population state and storing it in a population dataset; (c) detecting whether the population has reached a stable state; (d) if the population has reached the stable state: obtaining data representing the stable state, redetermining the selection pressures based on a selection pressure policy, and storing the data and the redetermined selection pressures in a stable state dataset; (e) determining whether one or more stopping criteria have been met; and repeating steps (a)-(e) until at least one of the stopping criteria is met.

20 Claims, 12 Drawing Sheets

(51) Int. Cl.
  *G16B 5/20* (2019.01)
  *C12M 1/34* (2006.01)
  *G05B 13/02* (2006.01)

(52) U.S. Cl.
  CPC ............ *C12M 41/36* (2013.01); *C12M 41/38* (2013.01); *G05B 13/0265* (2013.01); *G16B 5/20* (2019.02); *G16B 40/00* (2019.02)

(58) Field of Classification Search
  CPC ...... C12M 41/34; C12M 41/36; C12M 41/38; G05B 13/0265
  See application file for complete search history.

(56) References Cited

U.S. PATENT DOCUMENTS

| | | | | |
|---|---|---|---|---|
| 2002/0142321 | A1* | 10/2002 | Palsson | G16B 5/00 435/6.12 |
| 2007/0196815 | A1* | 8/2007 | Lappe | G01N 21/6458 382/120 |
| 2011/0029468 | A1* | 2/2011 | Fox | G16B 35/20 706/13 |
| 2013/0095566 | A1 | 4/2013 | Oltvai et al. | |
| 2014/0380528 | A1* | 12/2014 | Wood | C12N 15/113 800/298 |
| 2015/0315570 | A1* | 11/2015 | Zhao | G16C 20/60 506/14 |
| 2016/0348096 | A1* | 12/2016 | Liu | C12N 15/1024 |
| 2019/0153472 | A1* | 5/2019 | Shoulders | C12N 15/66 |
| 2019/0224681 | A1 | 7/2019 | Herzog et al. | |
| 2019/0276816 | A1* | 9/2019 | Liu | C12N 7/00 |
| 2019/0345487 | A1* | 11/2019 | Esvelt | C12N 15/1058 |
| 2020/0115705 | A1* | 4/2020 | Mason | C12N 1/20 |
| 2020/0183474 | A1 | 6/2020 | Kim et al. | |
| 2020/0199568 | A1* | 6/2020 | Bashor | C12N 1/20 |
| 2020/0393477 | A1* | 12/2020 | Davey | G01N 35/0099 |
| 2021/0292802 | A1* | 9/2021 | Konstantinidis | C12P 25/00 |

OTHER PUBLICATIONS

International Search Report and Written Opinion for International Patent Application No. PCT/US2021/048879, dated Dec. 22, 2021 (15 pages).

\* cited by examiner

| Algorithm Meta Control Procedure | |
|---|---|
| 1: $t = 0$ | |
| 2: $k = 0$ | |
| 3: Set time horizon $T$ | |
| 4: Set initial selection pressures $a_{init}$ | |
| 5: Initialize empty dataset $\mathcal{D}_t$ | |
| 6: Initialize empty dataset $\mathcal{D}_{ES}$ | |
| 7: repeat | |
| 8:   Poll system for new measurement of population state $s_k$ | |
| 9:   Add $s_k$ to dataset $\mathcal{D}_t$ | |
| 10:   detected = detectES($\mathcal{D}_t$) | ▷ e.g. Naive, ACF, Dickey-Fuller, etc. |
| 11:   if detected then | |
| 12:     Calculate ES state $S_t$ from $\mathcal{D}_t$ | |
| 13:     $a_t$ = policy($S_t$, $\mathcal{D}_{ES}$, $t$, $T$) | ▷ policy() depends on solution method |
| 14:     Apply selection pressure $a_t$ to the system | |
| 15:     Add $(S_t, a_t)$ to dataset $\mathcal{D}_{ES}$ | |
| 16:     $t = t + 1$ | |
| 17:     $k = 0$ | |
| 18:     Initialize empty dataset $\mathcal{D}_t$ | |
| 19:   else | |
| 20:     $k = k + 1$ | |
| 21:   end if | |
| 22: until $t = T$ | |

| Algorithm Sequential decision problem: Model-Based RL |
|---|
| 1: function POLICY($S_t$, $\mathcal{D}_{ES}$, $t$, $T$) |
| 2:     Update approximate dynamics model $\hat{f}_\theta(S,a)$ by supervised training with random $\{(S_t, a_t), S_{t+1}\}$ pairs from $\mathcal{D}_{ES}$ |
| 3:     Define utility function $U$ |
| 4:     $a_t = \pi_{MPC}(S_t; \hat{f}_\theta, U, t, T)$     ▷ Model-Predictive Control policy |
| 5:     return $a_t$ |
| 6: end function |

| Algorithm Optimization problem |
|---|
| 1: function POLICY($S_t$, $\mathcal{D}_{ES}$, $t$, $T$) |
| 2:     if $t = 0$ then |
| 3:         $a$ = generatePressures($S_t$, $T$)     ▷ e.g. Evolution Strategy, Bayesian Optimization |
| 4:     end if |
| 5:     return $a[t]$ |
| 6: end function |

FIG. 1D

| Method 300 | Model-Based RL |
|---|---|
1: Initialize approx. dynamics model $\hat{f}_\theta(s, a)$ by training with random $\{(s_t, a_t), s_{t+1}\}$ pairs from true dynamics $f$
2: Store $(s_t, a_t, s_{t+1})$ tuples in $\mathcal{D}_{\text{off}}$
3: Initialize empty dataset $\mathcal{D}_{\text{on}}$
4: Define reward function $R(s, a)$
5: repeat
6:    if $\mathcal{D}_{\text{on}}$ not empty then
7:       Train $\hat{f}_\theta$ on $\{\mathcal{D}_{\text{on}} \cup \mathcal{D}_{\text{off}}\}$
8:    end if
9:    Reset system; $t \leftarrow 0$.
10:   while $t <$ max_gens do
11:      $a_t = \pi_{\text{MPC}}(s_t; \hat{f}_\theta, R)$     ▷ Model-Predictive Control policy
12:      $s_{t+1} = f(a_t, s_t)$     ▷ Take action on real system.
13:      Add $(s_t, a_t, s_{t+1})$ to $\mathcal{D}_{\text{on}}$
14:      $t \leftarrow t + 1$
15:   end while
16: until max trials reached

FIG. 3

MACHINE LEARNING AND CONTROL SYSTEMS AND METHODS FOR LEARNING AND STEERING EVOLUTIONARY DYNAMICS

CROSS-REFERENCE TO RELATED APPLICATIONS

This application claims the benefit and priority under 35 U.S.C. § 119(e) of U.S. Provisional Patent Application No. 63/074,132 titled "Machine Learning and Control Systems and Methods for Learning and Steering Evolutionary Dynamics" and filed on Sep. 3, 2020, and claims priority and benefit under 35 U.S.C. § 119(e) of U.S. Provisional Patent Application No. 63/154,794, titled "Bioreactor Systems, and Related Methods and Apparatus" and filed on Feb. 28, 2021, each of which is hereby incorporated by reference herein in its entirety.

TECHNICAL FIELD

The present disclosure generally relates to systems and methods for using machine learning and control techniques (e.g., optimal control techniques) to learn and steer evolutionary dynamics.

BACKGROUND

Solving "sequential decision problems" involves using mathematical and statistical techniques to identify a set of inputs ("controls") to a system over a period of time such that an objective function is optimized or an optimality criterion is achieved. When the mapping f from a state of the system and a set of inputs to the system at a time t to a state of the system at a time t+1 is known, optimal control techniques may be applied to the system to achieve the optimality criterion. When the mapping f is unknown, reinforcement learning may be used to achieve the optimality criterion. With model-based reinforcement learning techniques, machine learning techniques are used to learn a model $\hat{f}$ of the system's mapping f and that model is used to identify the inputs to the system that achieve the optimality criterion. With model-free reinforcement learning techniques, the inputs to the system that achieve the optimality criterion are identified without learning a model $\hat{f}$ of the system's mapping f.

Optimizing features of biological systems is a major goal of a number of industries, including food, energy, materials, and medicine. In general, farmers try to maximize yields, biofuel developers try to maximize efficiency or minimize waste, materials companies try to optimize chemical ratios, and medical technologists try to minimize pathogenicity and virulence.

Current approaches to biological optimization include genetic modification and editing, artificial selection, and environment optimization. For example, biotechnology companies identify useful genes and move them to a new species, or delete undesirable genes that are already present. Breeders hand-pick the most desirable crops, and propagate them over and over again, accentuating a trait. Finally, AI companies use machine learning to fine-tune the optimal environment for an organism, identifying, e.g., an advantageous nitrogen to phosphorous ratio for a tomato.

However, each of these approaches has serious drawbacks. Genotyping is getting faster but still relatively slow and expensive, and compared to our ability to read a genetic sequence, we know next to nothing, a priori, about how that sequence maps to traits of interest. Even once we identify useful genes, the challenge remains to successfully transplant it or delete it without undesirable consequences. The most important and interesting traits, especially in more complex organisms, tend to be underpinned by vast networks of genes, making simple editing difficult or impossible for now. Much of the focus for gene editing has been on microbes, which have simple genomes and an in-built system for accepting genes from other organisms.

Artificial selection requires painstaking and brute force screening of individuals, selecting desirable ones, and repeating. Usually, we are selecting individual traits we think are going to be useful, like a larger corn cob. Often, these individual traits scale nonlinearly at the population level, such that a field of larger corn plants actually produces less overall corn. Further, by not changing the environment, we might be pushing the population away from a fitness optimum, such that, once the breeding program stops, the gains are reversed. Many of the early gains of GMOs were reversed in 20-30 years by evolution.

Finally, environmental optimization, while a promising new tool, is limited in how much it can be expected to improve organisms. By focusing on which features of the environment are best for a given organism, we are capped by the total potential of that organism's genotype. True biological optimization may be achieved through modification of both the environment and the genome.

SUMMARY

Fortunately, a potential alternative exists which can be controlled to solve these problems: evolution. All biological systems are both the products of evolution and constantly undergoing it. Evolution can push organisms in undesirable (from a human perspective) directions. For example, it can drive bacteria to become more virulent, or push crops to lower yields. Importantly, though, it does so in a much more robust way than current human techniques: it can select on the entire population, it uses random mutations to generate good genes that human engineers may be unable to identify, it incorporates genes that work well in concert with the rest of the organism, it is constantly checking the qualities of every single individual in a population, at every instance, with perfect precision, and it finds solutions that are stable against perturbations. In principle, if we could make evolution work for us, choosing those qualities that we desire, we would have the most powerful biological optimizing tool to date.

However, evolution is generally slow and unpredictable, and generally doesn't optimize for human goals. We rarely know what mutations will arise, what selection pressures new environments will impose, or which amongst many possible higher-fitness routes a population will pursue. The dynamics of evolutionary systems have long been considered far too complex to be precisely controlled by humans. Some embodiments of the techniques described in the present disclosure largely resolve this problem using machine learning and evolutionary modeling. In some embodiments, the systems described herein can learn the relationship between environmental conditions and evolutionary pathways, and institute an optimal control approach to drive an organismal population to an evolutionarily stable equilibrium that also maximizes some quantity of (human) interest.

According to an aspect of the present disclosure, a method for learning and steering evolutionary dynamics includes initializing a bioreactor, the initialized bioreactor including a population of evolving organisms; determining a set of selection pressures; (a) applying the set of selection pressures to the population; (b) determining the population state and storing the determined population state in a population dataset; (c) detecting whether the population has reached a stable state; (d) if the population has reached the stable state, obtaining stable state data representing the stable state, redetermining the set of selection pressures based on a selection pressure policy, and storing the stable state data and the redetermined set of selection pressures in a stable state dataset; (e) determining whether one or more stopping criteria have been met; and repeating steps (a)-(e) until at least one of the stopping criteria is met.

Other embodiments of this aspect include corresponding computer systems, apparatus, and computer programs recorded on one or more computer storage devices, each configured to perform the actions of the method. A system of one or more computers can be configured to perform particular actions by virtue of having software, firmware, hardware, or a combination of them installed on the system (e.g., instructions stored in one or more storage devices) that in operation causes or cause the system to perform the actions. One or more computer programs can be configured to perform particular actions by virtue of including instructions that, when executed by data processing apparatus, cause the apparatus to perform the actions.

The foregoing and other embodiments can each optionally include one or more of the following features, alone or in combination. In some embodiments, determining the set of selection pressures includes randomly determining the set of selection pressures. In some embodiments, determining the population state includes determining a morphology of the population. In some embodiments, determining the population state includes measuring at least one of: a yield of the population, a virulence of the population, a contagiousness of the population, a strength of a biomaterial produced by the population, a change in a measurable attribute of a biomaterial, a waste material production level of the population, an efficiency with which the population breaks down a material, a flavor or scent of an edible organism of the population, a competitive behavior of the population, an efficiency with which the population produce fuels, a water consumption level of the population, a nutrient consumption of the population, or fertilizer consumption of the population.

In some embodiments, detecting whether the population state has reached a stable state includes performing a time series analysis on the population dataset. In some embodiments, performing a time series analysis on the population dataset includes fitting a first degree polynomial to a leading window of a time series of population states in the population dataset; applying an autocorrelation function (ACF) to a leading window of the time series of population states; and/or fitting a regression model to the time series of population states and testing a null hypothesis that a unit root is present in the regression model. In some embodiments, determining the selection pressures includes applying at least one of a reinforcement learning policy or an optimization-based policy.

According to another aspect of the present disclosure, a system for learning and steering evolutionary dynamics includes one or more action modules operable to perform one or more actions affecting one or more attributes of an environment, the environment including a population of evolving organisms; one or more data collection modules operable to collect data indicating one or more characteristics of the population and/or the environment; and one or more computers and one or more storage devices storing instructions operable, when executed by the computers, to cause the computers to perform operations including the actions of the above-described method.

According to another aspect of the present disclosure, a system for learning and steering evolutionary dynamics includes one or more action modules operable to perform one or more actions affecting one or more attributes of an environment, the environment including a population of evolving organisms; one or more data collection modules operable to collect data indicating one or more characteristics of the population and/or the environment; and one or more computers and one or more storage devices storing instructions operable, when executed by the computers, to cause the computers to perform operations. The operations may include identifying an optimality metric, wherein a value of the optimality metric depends on at least one of the characteristics of the population, and wherein the value of the optimality metric does not satisfy an optimality criterion at an initial time t, (a) selecting at least one of the actions affecting at least one of the attributes of the environment, (b) controlling at least one of the action modules to perform the selected action(s), (c) controlling at least one of the data collection modules to collect data indicating a value of at least one of the characteristics of the population and/or environment, and repeating steps (a)-(c) until a stopping criterion is met. In each iteration of step (a), the at least one action may be selected based, at least in part, on the action(s) performed in one or more previous iterations of step (b) and the data collected in one or more previous iterations of step (c). The stopping criterion may be met when (1) a number of iterations of steps (a)-(c) reaches or exceeds a maximum number of iterations, or (2) the collected data indicate that the value of the optimality metric satisfies the optimality criterion.

Other embodiments of this aspect include corresponding methods, apparatus, and computer programs recorded on one or more computer storage devices, each configured to perform the operations of the system. A system of one or more computers can be configured to perform particular actions by virtue of having software, firmware, hardware, or a combination of them installed on the system (e.g., instructions stored in one or more storage devices) that in operation causes or cause the system to perform the operations. One or more computer programs can be configured to perform particular actions by virtue of including instructions that, when executed by data processing apparatus, cause the apparatus to perform the operations.

The foregoing and other embodiments can each optionally include one or more of the following features, alone or in combination. In some embodiments, the environment includes a photobioreactor; the population of evolving organisms includes a plurality of single-celled organisms; the attributes of the environment include temperature, pH, mixing speed, ratio of carbon dioxide to oxygen, and/or gas bubbling rate; the characteristics of the population and/or the environment include the temperature, the pH, the mixing speed, the ratio of carbon dioxide to oxygen, the gas bubbling rate, optical density, and/or an indicator of protein content; the optimality metric includes a level of protein content within algae cultivated in the bioreactor; and the optimality criterion is satisfied when the value of the optimality metric meets or exceeds a threshold value.

In some embodiments, the environment includes (1) a growth medium in which an oncolytic virus is cultivated and (2) one or more test wells, each test well including viable cancer cells and a drug candidate including the oncolytic virus; the population of evolving organisms includes the oncolytic virus; the attributes of the environment include one or more contents of the growth medium and/or one or more contents of the drug candidates; the characteristics of the population and/or the environment include the contents of the growth medium, the contents of the drug candidates, a viral load of the growth medium, one or more genetic characteristics of the virus, and/or one or more cell waste products in the test wells; the optimality metric includes a level of oncolytic efficacy of the virus; and the optimality criterion is satisfied when the level of oncolytic efficacy of the virus meets or exceeds a threshold value.

In some embodiments, the environment includes a biomaterial production reactor; the population of evolving organisms includes Escherichia coli ("E. coli") genetically modified to produce human albumin protein; the attributes of the environment include a temperature within the reactor, one or more contents of a growth medium within the reactor, a mixing rate within the reactor, a gas input to the reactor, a pressure within the reactor, and/or an environmental structure within the reactor; the characteristics of the population and/or the environment include a cell size of albumin protein within the reactor, a rate of cell death within the reactor, an optical density within the reactor, levels of one or more waste products within the reactor, and/or level of albumin output within the reactor; the optimality metric includes the level of albumin output; and the optimality criterion is satisfied when the level of albumin output of the E. coli meets or exceeds a threshold value.

In some embodiments, step (c) further includes training an approximate model of the evolutionary dynamics of the evolving organisms based, at least in part, on the action(s) previously performed and the data previously collected. In some embodiments, in each iteration of step (a), at least one action is selected based, at least in part, on an output of a model-predictive control (MPC) process performed using the approximate model.

The details of one or more embodiments of the subject matter described in this specification are set forth in the accompanying drawings and the description below. Other features, aspects, and advantages of the subject matter will become apparent from the description, the drawings, and the claims. The foregoing Summary, including the description of some embodiments, motivations therefor, and/or advantages thereof, is intended to assist the reader in understanding the present disclosure, and does not in any way limit the scope of any of the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 1B depicts an example of pseudocode for an embodiment of the method of FIG. 1A;

FIG. 1C depicts an example of pseudocode for a policy for selecting selection pressures, according to some embodiments;

FIG. 1D depicts an example of pseudocode for another policy for selecting selection pressures, according to some embodiments;

FIG. 3 depicts pseudocode of an example of a method for learning and steering evolutionary dynamics, according to some embodiments;

DETAILED DESCRIPTION

Figure 1A:
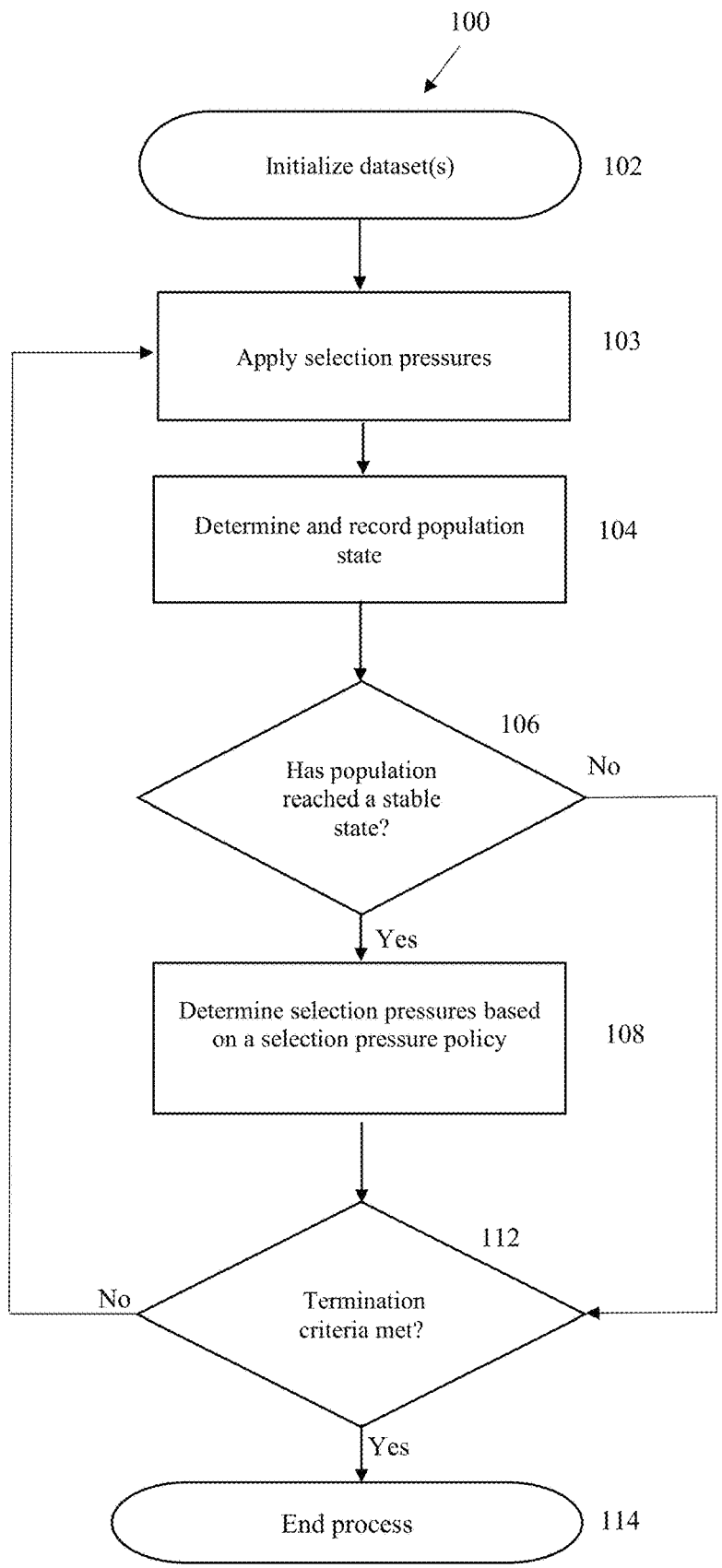
FIG. 1A depicts a flowchart of a method for learning and steering evolutionary dynamics, according to some embodiments.

The remainder of this disclosure proceeds as follows: first, some relevant principles are outlined. Second, some embodiments of control techniques (e.g., generalized optimal control techniques) for driving a system (e.g., a Darwinian system) to a target goal are described. Finally, some use cases are discussed.

Principles

In general, the state of an evolving population, e.g., a population state, can be a representation of the organisms currently within the population. This representation can be defined, for example, at the level of the genotype (e.g., gene frequencies) or the phenotype (e.g., summary statistics of observable traits). Some non-limiting examples of a population's observable traits may include growth rate, photosynthetic activity, among others. In practice, one can collect information about a population's state using suitable measurement techniques. In an example, for a population of E. Coli, genotypic state representations can be obtained using genetic sequencing while a phenotypic state representation may be obtained using spectroscopy.

Notions of evolutionary stability of a population state have been developed over the years, primarily in the field of evolutionary game theory, for a variety of settings. In one example, an original concept of an evolutionarily stable strategy ("ES strategy") refined the concept of a Nash Equilibrium to help explain evolutionary dynamics in two-strategy games for infinite populations. Since then, work has been done to extend the concept of evolutionary stability to arbitrary strategy sets in both discrete (e.g., a pure strategist) and continuous (e.g., a mixed strategist) models as well as for settings (e.g., small finite populations, random payoffs, etc.) where stochastic effects are non-negligible. In one example, a characteristic of a system embodying any notion of stability can include a tendency of said system to return to a state following perturbation from that state.

In theory, a population state is stable if the population will return to that state (with certainty) following perturbation. In practical applications, the stability of a population's state can be difficult to guarantee as all related assumptions do not necessarily hold. In other words, in practice, it may not be possible to guarantee that a population is in a stable state, or to determine with certainty that a population's state is stable. However, in practice, the assumptions that can be made can often be sufficiently accurate such that it is possible to determine (with high probability) whether a population is in a stable state. In other words, it is possible to determine (with high probability) whether a population will return to its prior state following perturbation. Some non-limiting examples of techniques for determining whether a population is in a stable state are described below. A stable state of a population may be referred to herein as an "evolutionarily stable state," "ES state," or simply "stable state."

The evolution of a population of organisms may be influenced by "selection pressures" applied to the population. Selection pressures can include factors that influence or contribute to the variation of one or more organisms within a population. In some examples, selection pressures can be applied to (e.g., imposed on) a population by the population's environment. For example, selection pressures applied to (e.g., experienced by or imposed on) a population can include temperature, light exposure, chamber pressure, input feeds/nutrients, population density, among others. In some examples, selection pressures can influence certain phenotypes of a given population, e.g., some organisms of a certain phenotype can have an advantage over other organisms within a population subjected to a particular set of selection pressures. As selection pressures are further applied over time, these pressures can affect (e.g., steer) the evolution of the population.

In some examples, humans may have actual goals in relation to other organisms within a population. In one example, they may want their cows to produce more milk, their spiders to produce more silk, and bacteria to be less contagious.

Most organisms do not possess actual goals. They operate blindly according to programmed rules. However, as a result of natural selection, organisms appear as though they have goals. For example, the gazelle appears as though it does not want to be eaten by the lion, and the lion appears as though it wants to eat the gazelle.

More precisely, as a result of natural selection, organisms appear as if trying to maximize a quantity known as inclusive fitness. Inclusive fitness is the sum of an individual's adult number of offspring after it has been 'stripped of all components which can be considered as due to the individual's social environment,' and a weighted sum of the 'quantities of harm and benefit which the individual himself causes' to the offspring numbers of others. The weightings are degrees of relatedness. Relatedness is a measure of genetic similarity between two individuals (r=1 for identical twins, r=0 for random population member, including possibility of self in finite populations).

It can be proven, under some assumptions, that organisms maximize their inclusive fitness at equilibrium, e.g., a stable state. Accordingly, we can treat organisms as though they have goals, where their goal is to maximize inclusive fitness, and accurately predict their behavior.

A Method for Learning and Steering Evolutionary Dynamics

Referring to FIG. 1, a method 100 for learning and steering evolutionary dynamics is presented. In some embodiments, the method 100 involves making changes to the environment of a population of organisms in accordance with a policy, thereby controlling the selection pressures on the population and steering the population's evolution. In some embodiments, the policy for controlling the selection pressures on the population may be based on evolutionary models and/or machine learning. In some embodiments, the population's environment may be located within a bioreactor, which may facilitate monitoring and/or control of the environment. In some embodiments, the method 100 may be used to control the population's evolution, such that the population reaches a stable state in which the value of an objective function (e.g., a function having a value that depends on attributes or activities of the population) satisfies one or more performance criteria (e.g., the value of the goal function is maximized or approximately maximized, the value of the goal function exceeds a specified threshold value, etc.).

Still referring to FIG. 1, the method 100 for learning and steering evolutionary dynamics may include steps 102-114, each of which is described in further detail below.

The method 100, in a step 102, can include initializing one or more datasets. In some embodiments, the dataset(s) initialized in step 102 may include a population dataset D, which may indicate (e.g., represent) one or more states of the population of organisms within the bioreactor. Some non-limiting examples of techniques for measuring the state of a population are described below. As used herein, the notation $D_t$ may refer to a portion of the population dataset D that indicates the state of the population at a particular time t or during a particular period of the population's evolution. For example, the notation $D_0$ may refer to one or more states of the population (e.g., a time-series of states of the population) during a first period (period 0) in which selection pressures (e.g., initial selection pressures) $a_{init}$ are applied to the population. Likewise, the notation $D_1$ may refer to one or more states of the population (e.g., a time-series of states of the population) during a second period (period 1) in which selection pressures (e.g., policy-specified selection pressures) $a_1$ are applied to the population, the notation $D_2$ may refer to one or more states of the population during a third period (period 2) in which selection pressures (e.g., policy-specified selection pressures) $a_2$ are applied to the population, and so on.

As used herein, the notation $s_k$ may refer to the state of a population at a particular time k or during a particular phase (e.g., generation) k of the population's evolution. In some examples, the index k may indicate a particular time associated with the corresponding measurement of the population's state (e.g., the amount of time elapsed since the bioreactor was initialized, since the method 100 was initiated, or since detection of a particular stable state; the date/time at which the state of the population was recorded, etc.). In some embodiments, the index k may indicate a temporal ordering of the corresponding measurements of the population's state (e.g., the k-th measurement of the population's state since the bioreactor was initialized, since the method 100 was initiated, or since detection of a particular stable state, etc.).

In some embodiments, initializing a population dataset can include setting the period index t and the time index k to 0. In some embodiments, initializing a population dataset can include initializing the dataset D to be empty (e.g., no population data recorded at initialization).

In some embodiments, the dataset(s) initialized in step 102 may include a stable state dataset $D_{ES}$, which is sometimes referred to herein as an "evolutionarily stable state"

dataset or "stable state" dataset. In some examples, initializing the stable state dataset $D_{ES}$ can include setting the stable state dataset $D_{ES}$ to empty (e.g., no data at initialization). In some embodiments, the stable state dataset $D_{ES}$, may indicate (e.g., represent) stable states exhibited by the population and/or the selection pressures that caused the population to evolve into those stable states. As used herein, a set of selection pressures may be said to "cause" a population to evolve into a stable state if the application of that set of selection pressures precedes or coincides with the evolution of the population into the stable state. In some embodiments, the data stored in the stable state dataset $D_{ES}$ can include a sequence (e.g., time series) of pairs of stable states $S_t$ and selection pressures $a_t$ applied to the population after reaching the stable state $S_t$ (e.g., selection pressures $a_t$ that cause the population to evolve into a next stable state $S_{t+1}$).

In some embodiments, step 102 can include initializing a stable state threshold T (sometimes referred to herein as a "horizon time" T), which may indicate the maximum number of distinct stable states the population will be permitted to reach before terminating the method 100.

Referring to FIG. 1B, pseudocode 150 for an embodiment of the method 100 is shown. In some embodiments, step 102 of the method 100 may include performing the actions described in lines 1-3 and 5-6 of the pseudocode 150.

Referring again to FIG. 1A, in a step 103, a set of selection pressures $a_t$ may be applied to the population in the bioreactor. As used herein, the notation a may refer generally to the selection pressures exerted on the population, and the notation $a_t$ may refer to the selection pressures exerted on the population at a particular time t or during a particular period of the population's evolution. For example, the notations $a_0$, $a_1$, and $a_2$ may refer to respective sets of selection pressures exerted on the population during first, second, and third periods of the population's evolution.

In some embodiments, the selection pressures $a_t$ may be applied by controlling the environmental conditions within the bioreactor. In an example, apply selection pressures to the population within the bioreactor can include setting the temperature within the bioreactor; setting the pH within the bioreactor; setting the mixing speed of a fluid within the bioreactor; setting the ratio(s) of two or more gases within the bioreactor (e.g., the ratio of carbon dioxide to oxygen); setting the gas bubbling rate within the bioreactor; providing a particular growth medium for the population; setting an ambient pressure with the bioreactor; providing an environmental structure within the reactor (e.g., a lattice); controlling the types, amounts, and/or rates of inputs (e.g., feed, water, light, fluid, gas, etc.) provided to the bioreactor's population; controlling the rate at which outputs (e.g., waste) are removed from the bioreactor, etc. In some examples, the initial selection pressures can be informed (e.g., selected in accordance with or based on a specific rationale) or non-informed (e.g., generated randomly).

In some embodiments, applying the selection pressures $a_t$ to the population may include maintaining the selection pressures $a_t$ on the population (e.g., maintaining the environmental conditions within the bioreactor). In some cases, open-loop and/or closed-loop control techniques may be used to maintain conditions within the bioreactor. In an example, an open loop control technique can include setting the speed of a bioreactor component (e.g., the stirring speed of a stir bar, which may be specified in revolutions per minute (RPM)) without measuring the component's speed to determine whether it matches the nominal setting. In one example, a closed-loop control technique can include setting, measuring, and adjusting the value of a bioreactor parameter (e.g., temperature) to facilitate stable maintenance of that parameter at the specified value. In some examples, the environmental attributes of interest (e.g., selection pressures) may be measured intermittently (e.g., periodically), and the bioreactor's inputs and/or outputs may be adjusted to maintain those environmental attributes at the desired levels. Any suitable techniques and/or devices may be used to measure the environmental attributes of interest. For example, the temperature within the bioreactor may be measured with a temperature probe; the pH within the bioreactor may be measured with a pH probe or with sensor dots and spectroscopy; the mixing speed of a fluid or fluids within the bioreactor may be controlled using a stir bar; the ratio of gases within the bioreactor may be measured with spectroscopy, or measured and controlled with a gas mixing system including flow rate sensors; the gas bubbling rate within the bioreactor may be controlled with gas mixing system including flow rate sensors; the contents of a growth medium within the bioreactor may be measured using spectroscopic analysis and/or controlled by selecting the growth medium's substrate composition; gas input to the bioreactor may be controlled with a gas mixing system including a flow rate sensor; pressure with the bioreactor may be measured using a pressure gauge; etc.

Referring to FIG. 1B, step 103 of the method 100 may include performing the actions described in line 4 and 14 of the pseudocode 150.

Referring again to FIG. 1A, in a step 104, the method can include determining (e.g., measuring) and recording the population state. In some embodiments, determining population state can include measuring, either directly or by proxy, the population's cell morphology, e.g., using cameras, computer vision tools, and/or any other suitable type of sensor or tool. In some examples, measuring population state can include measuring attributes of the population's environment. Some non-limiting examples of attributes of a population's environment are described above. In some embodiments, determining population state can include measuring the optical density of the population (e.g., with an optical density sensor), measuring an indicator of protein content of the population (e.g., measuring the concentration of a fluorophore using fluorescence or multi-wavelength 2D or 3D fluorescence, determining the quantity and concentration of an expressed protein using fluorescence spectroscopy, etc.), measuring a viral load of the population's growth medium (e.g., through PCR analysis), determining one or more genetic characteristics of the population (e.g., by identifying known genetic markers), measuring levels of one or more cell waste products (e.g., cell waste amino acid) of the population (e.g., with fluorescence spectroscopy or other spectroscopic analysis of the waste product), measuring cell size of a protein (e.g., albumin protein) produced by the population (e.g., with microscopy and/or computer vision techniques), measuring the level of protein output (e.g., albumin output) within the reactor (e.g., through MIR spectroscopy or a targeted biosensor), measuring a rate of cell death (e.g. apoptosis) within the population (e.g., by using spectroscopic techniques to measure products released during lysis), etc.

In some embodiments, a population state can include the population having an optical density within an expected (e.g., user-specified) range, the population having a protein content within an expected (e.g., user-specified) range, a population having a specific genetic characteristic, the population producing a specific waste product, the population having cell sizes (e.g., average cell sizes) within a specific cell size range, the population producing a specific level of protein output, the population having a cell death rate within a specific range, among other population state examples.

In some embodiments, measuring population state can include, without limitation, directly or indirectly measuring yields of biological populations, virulence, contagiousness of viral populations, strength or any other measurable attribute of a biomaterial, waste material production (e.g., plastic, gold) of a member of the population (e.g., an organism), the efficiency with which a member of the population breaks down a material (e.g., oil, plastic), the flavor or scent of a member of edible population of organisms, the competitive behavior of a member of the population, the efficiency with which a member of the population produces fuel (e.g., a more efficient biofuel), the water, nutrient and/or fertilizer consumption of a member of the population, etc.

In some embodiments, the measurement of the population's state can be represented as $s_k$, where k can represent a generation index (e.g., a number of generations since most recent stable state). In the same example, the measurement of the population's state may be recorded by adding $s_k$ to the population dataset $D_t$.

In some embodiments, prior to determining and recording the population state, the selection pressures $a_t$ may be maintained for at least a minimum time period. During that time period, the population may evolve. The minimum time period may be determined using any suitable technique. In some cases, the minimum time period may be a user-specified time period (e.g., a time period between one second and one year or longer). In some cases, the minimum time period may be the estimated life span of one or more generations of the population.

Referring to FIG. 1B, step 104 of the method 100 may include performing the actions described in lines 8-9 of the pseudocode 150.

Referring again to FIG. 1A, in a step 106, the method can include determining whether the population state has reached a stable state. In some embodiments, determining (e.g., detecting) whether a population state has reached a stable state can involve performing a time series analysis on the population dataset $D_t$. In this context, time series analysis of the population dataset may be useful because, in general, a population's state is stable when data describing the population's state remain constant (e.g., do not change, or exhibit fluctuations within acceptable bounds) over time. In one example, a statistical and slightly more rigorous test for population state stability is "stationarity." In an example, the population's state may be determined to be stable if the statistical properties (e.g., mean, variance, etc.) of the time series of population state measurements are stationary (e.g., the statistical properties of the time series do not change over time, or any fluctuations in these statistical properties remain within specified bounds). (One of ordinary skill in the art will appreciate that the stationarity of a time series increases as the changes in the statistical properties of the time series decrease, and vice versa.)

Some non-limiting examples of techniques for determining whether a population state is stable can include one or more of the following time series analysis techniques: naïve stability detection, autocorrelation, and/or Dickey-Fuller detection.

In one example, performing naïve stable state detection can include fitting a function (e.g., a polynomial, for example, a first or second degree polynomial) to a leading window of the time series of population states $D_t$. The window may be of any suitable size (e.g., 2-10 or more measurements of population state $s_k$). In the same example, the coefficient of the highest order term of the fit can describe the approximate velocity of the population state over the leading window. In the same example, if the absolute value of the coefficient is sufficiently low (e.g., less than a specified threshold) for a sufficient number of time steps k (e.g., 2-5 or more time steps), then the population is determined to be in a stable state (e.g., evolutionarily stable state).

In another example, performing autocorrelation-based stable state detection can include applying an autocorrelation function (ACF) to a leading window of the time series of population states $D_t$. The window may be of any suitable size (e.g., 2-10 or more measurements of population state $s_k$). One of ordinary skill in the art will appreciate that autocorrelation values for a stationary time series tend to degrade quickly to zero and/or to oscillate around zero over time. Thus, in some embodiments, if the autocorrelation values for a leading window of the time series of measurements of population state $s_k$ degrade to zero and/or oscillate around zero, the population is determined to be in a stable state.

In yet another example, performing Dickey-Fuller based stable state detection can include fitting a regression model (e.g., an autoregression model) to the time series of population states $D_t$ and testing the null hypothesis that a unit root is present in the model. In some embodiments, if the null hypothesis is rejected, the population is determined to be in a stable state. Alternatively, if the null hypothesis is not rejected, the population may be determined to be in an unstable state, or one or more other techniques for determining whether the population state is stable may be applied.

Referring to FIG. 1B, step 106 of the method 100 may include performing the actions described in line 10 of the pseudocode 150.

Referring again to FIG. 1A, if the population's state has been determined to be stable, a step 108 may be performed. In step 108, the current stable state of the population, represented herein as $S_t$, can be determined based on the population state dataset $D_t$. Any suitable technique may be used to determine the current stable state $S_t$. In some embodiments, the population's current state $s_k$ may be selected as the current stable state $S_t$. In some embodiments, the current stable state $S_t$ may be determined by combining two or more previous states of the population (e.g., $s_k$, $s_{k-1}$, and so on). Any suitable combination of two or more previous states of the population may be used, e.g., an average or weighted average of the previous states.

Still referring to step 108, the next set of selection pressures $a_t$ may be determined. In some embodiments, the selection pressures $a_t$ can be determined based on the current stable state $S_t$, the stable state dataset $D_{ES}$, time index t and horizon time T. In some embodiments, the selection pressures $a_t$ may be determined by applying a selection pressure policy to the current stable state $S_t$, the stable state dataset $D_{ES}$, and any other suitable data (e.g., period index t and horizon time T). Some non-limiting examples of selection pressure policies are described below.

In some embodiments, the current stable state $S_t$ and the next set of selection pressures $a_t$ can be added to the stable state dataset $D_{ES}$. For example, a tuple ($S_t$, $a_t$) may be added to the stable state dataset $D_{ES}$. In some embodiments, additional information may be stored in the stable state dataset $D_{ES}$ in connection with the current stable state $S_t$. For example, the value $V_t$ of an objective function U may be calculated based on the current stable state, and a tuple ($S_t$, $V_t$, $a_t$) may be stored in the stable state dataset $D_{ES}$.

Any suitable objective function U may be used, and the value of the objective function may be calculated using any suitable data (e.g., the current stable state $S_t$, other stable states, other data external to the population states, etc.). For example, the value of the objective function can be determined based on biological information related to the population (e.g., dimensions of the population state) as well as information external to the population state (e.g., the cost of consumables). In some embodiments, the value of the objective function may indicate the extent to which the current stable state satisfies one or more performance criteria.

In one example, the method 100 can be configured to reach a stable state $S_t^+$ such that $U(S_t^+) > \alpha > U(S_0)$ where $S_0$ is the initial stable population state and $\alpha$ is a predefined threshold for success. As described above, the populations can reach stable states under fixed selection pressures. Therefore, applying a new set of selection pressures $a_t$ to a population currently in a stable state $S_t$ can move the population to a new stable state $S_{t+1}$. If the selection pressures are chosen in accordance with a suitable selection pressure policy, the application of those selection pressures to the population may lead to a state $S_t^+$ such that $U(S_t^+) > \alpha > U(S_0)$ where $S_0$ is the initial stable state of the population. In some embodiments, the selection pressure policy is a mapping from stable states S to selection pressures a. In some embodiments, the selection pressure policy (e.g., the task of choosing selection pressures following the settling of a population state into a stable state in order to move the population state to a different stable state that enhances (e.g., optimizes) the value of the objective function U) may be based on a solution to a sequential decision problem and/or on a solution to an optimization problem.

In some embodiments, the task of selecting a set of selection pressures $a_t$ can be framed as the task of solving a sequential decision problem. Each time the population reaches a stable state $S_t$, the system can attempt to identify a set of selection pressures a such that imposing selection pressures a yields the highest probability, for all a∈A (where A is the set of all unique selection pressures), of leading the population to a state $S_{t'}$ where t'>t and $U(S_{t'}) > \alpha > U(S_0)$.

In some embodiments, the search for a suitable set of selection pressures a can be unconstrained. For example, the system can evaluate each possible set of selection pressures a∈A until the set of selection pressures most likely to drive the population into a state $S_{t'}$ is identified. In some embodiments, constraints may be imposed on the search. For example, the number of stable states that the population is permitted to visit before a solution is found can be constrained, the number of times the population state can be reset to its initial stable state $S_0$ can be constrained, etc.

In some embodiments, evolutionary theory may be applied to enhance the optimality of the selection pressure policy. One of ordinary skill in the art will appreciate that evolutionary dynamics are such that the above-described sequential decision problem generally satisfies the properties of a Markov Decision Process. In some embodiments, suitable techniques for solving the above-described sequential decision problem can include reinforcement learning (RL) techniques (e.g., model-based or model-free RL techniques).

Referring to FIG. 1C, an example of a model-based RL policy for selecting a next set of selection pressures $a_t$ is illustrated. In general, a model-based RL policy may involve explicitly learning an approximate dynamics model of an evolutionary system, which can implicitly involve learning about the evolutionary dynamics of the population. As shown in the example of FIG. 1C, input to the model-based RL selection pressure policy may include, for example, a current stable state S (e.g., $S_t$), the stable state dataset $D_{ES}$, period index t and horizon time T. In some embodiments, a model of the population's evolutionary dynamic can be updated (e.g., by performing supervised training with tuples (($S_t$, $a_t$), $S_{t+1}$) generated from the stable state population dataset $D_{ES}$. The tuples may be randomly selected. In some embodiments, a model-predictive control (MPC) policy can be used to determine the next set of selection pressures $a_t$ based on, for example, the current stable state S (e.g., $S_t$), the evolutionary dynamics model, the utility function U, the period index t, and the time horizon T.

Another example of a model-based RL policy for selecting a next set of selection pressures $a_t$ is illustrated in FIG. 3 and described below.

In some cases, using a model-based RL policy (or a specific type of model-based RL policy) to select a next set of selection pressures $a_t$ may be impractical or infeasible. For example, the evolutionary dynamics model for the system may be highly uncertain, and/or the population state space may be highly complex. In such cases, the use of dynamic programming and value/policy iteration may be impractical or infeasible.

In some cases, a model-free RL policy for selecting a next set of selection pressures $a_t$ may be used. Applying the model-free RL policy can include directly learning a policy function or a state-action value function from which a policy is extracted, without learning a dynamics model and/or a reward function.

In some embodiments, the task of selecting a set of selection pressures $a_t$ can be framed as the task of solving an optimization problem, such that the "best possible" solution among a set of feasible solutions is determined. As described above, the system moves from one stable state to another stable state in response to the application of a new set of selection pressure $a_t$. Thus, given an initial stable state $S_0$, the trajectory of states visited before resetting the population to its initial state can be fully defined by $S_0$ and the sequence of chosen selection pressures $a = \{a_0, \ldots, a_{T-1}\}$ where T is the total number of stable states visited by the population after the initial stable state. Thus, the objective can be framed as a function of the initial stable state $S_0$ and selection pressure sequence a. In general, $S_0$ can be chosen and thus the problem of finding the appropriate selection pressures can be framed as an optimization problem over the input variable a.

Referring to FIG. 1D, an example of an optimization-based policy for selecting a next set of selection pressures $a_t$ is illustrated. In some embodiments, applying the optimization-based policy may include applying evolutionary strategies and/or Bayesian optimization. In many cases, solutions for optimization problems can be derivative free, meaning that they do not require information about the derivative of the objective function (or learned approximation of the objective function) to find optimal solutions. In one embodiment, selection pressures can be randomly chosen from a set of pre-defined options using any suitable technique.

Referring again to FIG. 1B, step 108 of the method 100 may include reinitializing the population state dataset D and associated indices in preparation for the application of the new set of selection pressures $a_t$. For example, the period index t may be incremented (t=t+1) and the time index k may be reset to 0. In some embodiments, upon reinitialization, the next population dataset $D_t$ can be empty (e.g., no population data recorded).

Referring to FIG. 1B, step 108 of the method 100 may include performing the actions described in lines 11-13 and 15-18 of the pseudocode 150.

Referring again to FIG. 1A, after performing step 108, the method may proceed to step 112. Alternatively, if the population has not reached a stable state at step 106, the method may proceed directly to step 112 without step 108 being performed.

In a step 112, the method can include determining whether termination criteria met has been met. In an example, determining whether termination criteria has been met can include determining whether the horizon time T has been reached and determining whether the value of the objective function $U(S_t)$ exceeds a threshold $\alpha$. If none of the termination criteria have been reached, the method can return to step 103. If any of the termination criteria have been reached, the method can terminate.

In some embodiments, in a system with multiple bioreactors, the method 100 can be applied independently to the population in each bioreactor.

A System for Learning and Steering Evolutionary Dynamics

Figure 2:
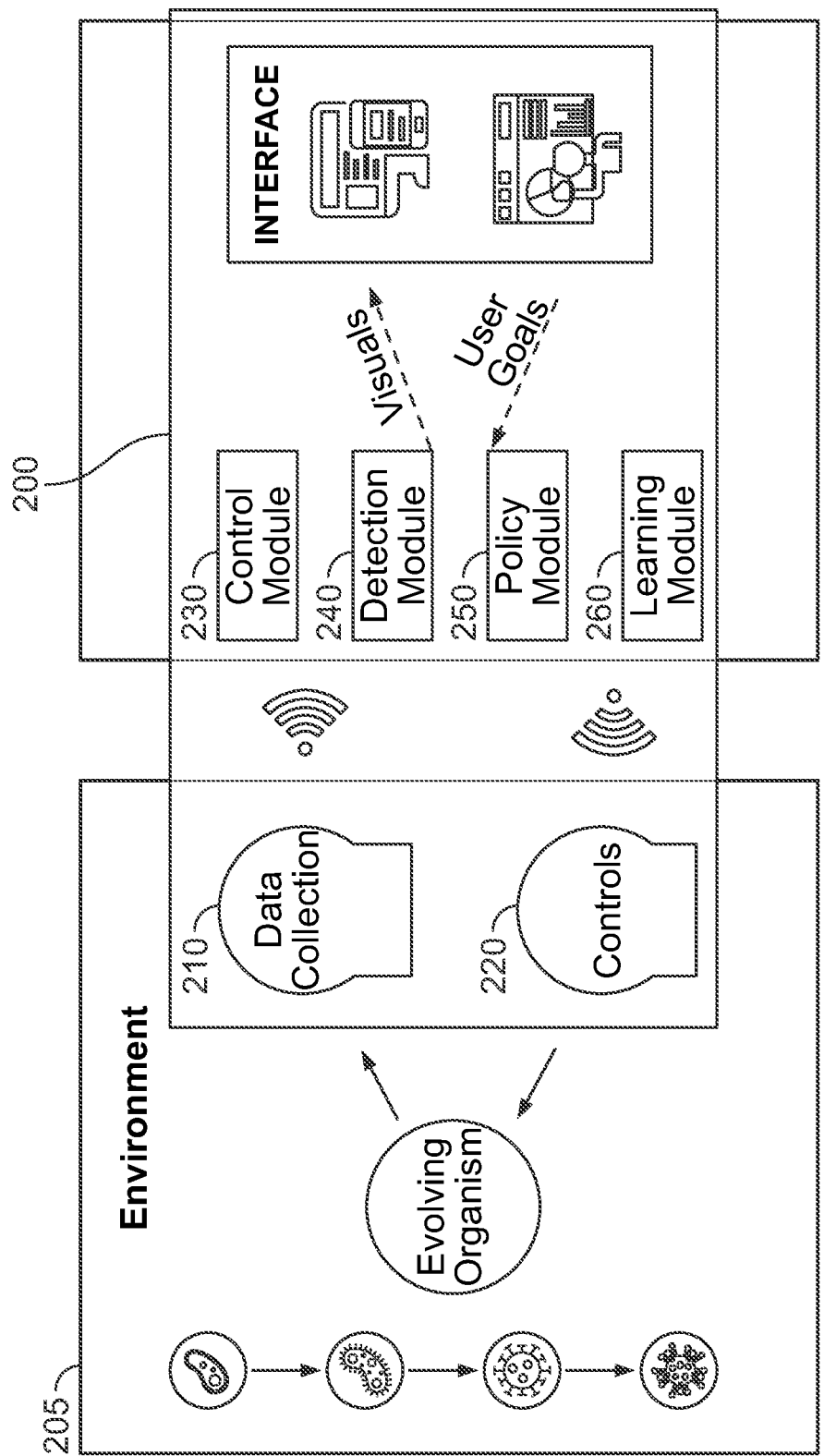
FIG. 2 depicts a block diagram of a system for learning and steering evolutionary dynamics, according to some embodiments.

Referring to FIG. 2, a system 200 may perform the method 100 to learn and steer evolutionary dynamics of a population of entities (e.g., organisms) within a environment (e.g., a bioreactor). In some embodiments, the system 200 can include a closed-loop data-in controls-out system. In some embodiments, the system 200 can include one or more data collection modules 210, one or more controls 220, one or more control modules 230, one or more detection modules 240, one or more policy modules 250, and/or one or more learning modules 260.

In some embodiments, the data collection module 210 may include one or more sensors (e.g. temperature probe, sensor dots, flow rate sensor, pressure gauge, optical density sensor, fluorescence sensor, PCR analysis, microscope, machine vision tools, targeted biosensor, photodiodes, cameras, pH probes, thermometers, etc.) operable to collect data on the population (e.g. color, density, nutrient ratios, apoptosis rates, etc.) and/or the environment (e.g. temperature, brightness, humidity, etc.). Any suitable sensors may be used. In some embodiments, the data collection modules 210 may transfer the collected data to one or more processing devices, which may convert the data into a format compatible with the method 100.

In some embodiments, the modules 230-260 may predict and/or control the changes in the dependent variables of the environment 205 (e.g., bioreactor) that will result from taking an action with respect to the environment 205 (e.g., applying selection pressure $a_t$ to the population in the environment) (e.g., changing the values of one or more controllable environmental parameters). In some embodiments, the system 200 may use the modules 230-260 to implement the steps described in the method 100 of FIG. 1. In some examples, the system 200 may use the policy module 250 during the step 108 of the method 100 to determine an action to be taken with respect to the environment 205, e.g., to determine apply the next set of selection pressures $a_t$ to apply to the population within the environment 205. In some examples, the system 200 may use the detection module 240 during the step 106 of the method 100 to determine whether the population has reached a stable state (e.g., as described above in detail with reference to step 106). In some examples, the system 200 may use the controls 220 to apply selection pressures $a_t$ to the bioreactor at the step 103 of the method 100 (e.g., as described above in detail with reference to step 103). In some examples, the system 200 may use the learning module 260 to perform reinforcement learning (RL) operations. In some embodiments, the control module 230 can control the other components of the system 200 iteratively perform the steps of method 100.

The ability to quickly and effectively modify organismal traits using the methods described herein, are, in part, a function of the scale and accuracy of evolutionary data feeding the algorithms, and the tightness with which selection pressures can be controlled. Machine learning methods can generally learn more efficiently and/or effectively the more data they have, and the more accurately the data represents the system's state. The effectiveness of the controls to convert learned dynamics into successful steering can be in part of a function of how tightly and accurately those controls can be set (e.g. temperature within, for example, 30 degrees C. plus or minus 0.01 degree). In particular, increasing the number of independently evolving populations on which data can be collected and controls exerted increases the power of the approach. In view of the above, in some embodiments, the system 200 can include multiple bioreactors, e.g., a massively parallel bioreactor system, which can (1) cultivate a large number (e.g., tens, hundreds, thousands, etc.) of independently evolving populations of organisms (e.g., in continuous liquid culture), (2) take real-time and/or near real-time measurements of various components of the population states (e.g., including measurements of the organisms, populations, and environments), and (3) finely control the selection pressures in each bioreactor in real-time and/or near-real time. In an example, the multi-bioreactor system 200 can generate higher quantity and quality of data, provide more precise controls, and significantly accelerate the process of learning and steering evolution.

In some examples, the system 200 (e.g., provided the sensors can be species agnostic) can be configured to perform the methods described herein to solve a wide variety of problems and/or can be used for a wide variety of organisms (e.g., including yeast, bacteria, mammalian cell lines, and filamentous fungi, among others). In some embodiments, the system 200 can be configured to increase the yield of a molecule (e.g. protein) or cell, increase secretion, drive changes in morphology, drive changes in material properties of cellular products (e.g. pigment, strength), etc. In some embodiments, the system 200 can be referred to herein as a reactor, bioreactor and/or an evolution reactor, among other terms.

In some embodiments, the system 200 is operated in-house. For example, the "user" could be a provider or operator of the system 200. For example, the provider or operator of the system 200 could have the goal of evolving a yeast that produces heme for meat alternatives, and could perform the method 100 on in-house yeast reactors, and later sell its genome or other valuable product to other companies.

Exemplary Method for Learning and Steering Evolutionary Dynamics

Some specific embodiments of the above-described method 100 is now described. These embodiments are described by way of example and are not limiting.

In an example, taking US to mean those humans possessing a goal function with respect to an organism, and the CROP to be the organism, the foregoing observations can be expressed formally as follows:

Our utility function is $U^{(US)}(s)$ which maps from a given state of our system to the expected discounted return where our return might be, for example, yield over cost. Any suitable cost metric be used, e.g., amount of energy expended, amount of another resource expended, etc. $U^{*(US)}$(s) represents our optimal utility function over a policy set, π, where $$U^{*(US)}(s) = \max_\pi U^{(US)}_\pi(s) \qquad (1)$$

$$\text{Return}_{US} = \frac{\text{Yield}}{\text{Cost}}$$

Any suitable measure of return may be used including, without limitation, pathogenicity. The CROP's utility function is $U^{(CROP)}(s)$ which maps from a given state of our system to the expected discounted return where their return is inclusive fitness:

Return$_{CROP}$=InclusiveFitness

There is no general expression for inclusive fitness. But in a very large population (e.g., a population of nearly infinite size) subdivided into social groups of size N, the inclusive fitness $u_{IF}$ of an individual playing y, in a group $x_{-i}$, with population incumbent x can be expressed as follows:

$$u_{IF}(y,x)=w(x,x^{N-1},1_x)+w(y,x_{-i},1_x)-w(x,x_{-i},1_x)+r(y,x)$$
$$\Sigma_{j\neq i}(w(x,x_{-i-j},y,1_x)-w(x,x_{-i-j},x,1_x)), \qquad (2)$$

where r (y, x) is the relatedness from the perspective of a y player in a population monomorphic for x and w(x, X, $1_x$) is the mean offspring number (neighbor-modulated fitness) of an individual playing x in a patch of individuals playing strategies expressed by the vector X in a population monomorphic for x.

The available actions in the system are:
US: Changes to environments, and
CROP: Strategies which maximize inclusive fitness (IF) in an environment.

Let $\pi_{(CROP)}$ be the policy associated with a crop population whose goal is to maximize their inclusive fitness. Then we can let f: $\mathbb{R}^n \to \mathbb{R}$ be a function mapping their policy (or strategies) to a quantity of interest (such as yield):

Yield=$f(\pi^{(CROP)})$.

Let $\pi^{(US)}(s)$ be our policy for choosing environments given the state. Then we can let g: $\mathbb{R}^n \to \mathbb{R}$ be a function mapping our policy (or strategies) to our operational cost:

Cost=$g(\pi(s))$.

Therefore, we denote the policy which maximizes $U^{(US)}$ as $\pi^*(s)$ and define it as $$\pi^*(s) =_\pi^{arg\ max}(U_\pi^{(US)}).$$

Note that $\pi^{(CROP)}$ is a function of the fitness landscape, which is in turn a function of the environment. Therefore, our policy, $\pi^*(s)$, works by indirectly affecting the policy of the CROP. A key insight here is that this approach generally has the most potential value when our utility function is a function, however indirectly, of organismal policy.

Referring to FIG. 3, a method 300 (e.g., an optimal control method) for learning and steering (e.g., controlling) evolutionary dynamics is presented in a pseudo-code form. In some embodiments, the method 300 uses a policy informed by evolutionary models and machine learning to make changes to an environment in order to improve (e.g., maximize) $U_\pi^{(US)}$.

The principle behind this approach is that two factors determine the direction of evolution: environmental conditions and available mutations. In a desert environment, if a mutation for drought resistance arises, it will most likely spread through the population. Of course, mutations arise randomly, and we are still decades off from understanding the relationship between genotype and phenotype well enough to utilize the mutation component of evolution. Environmental conditions, however, can be easily manipulated.

The power of this approach comes from the fact that, though our utility function and the CROP utility function will not be directly aligned, we can move the CROP policy to a position that better satisfies our utility function simply by changing the environment.

FIG. 3 shows an example of a method 300 which combines manipulations of the environment, with readings of the evolutionary response, to learn those environments (or sequences of environments) which lead organisms to maximize (or approximately maximize) the human-level goal function.

Consider the general task of doing control given a dynamical system (e.g. directing the end-effector of a robotic arm to a desired position in space). If we have analytical expressions for the dynamics of our system we can often derive the Jacobian, relating the inputs to our dynamical system (e.g. joint torque) to the outputs (e.g. position of end-effector in space). From here we can do control using inverse kinematics, obtaining appropriate inputs given a desired output. However, there are many systems for which inverting the forward kinematics is difficult or where the dynamics are not known explicitly. In these cases we turn to approximate solution methods. Some embodiments of the systems and methods described in the present disclosure may be used to do control on the evolution of a population, a highly non-linear dynamical system without an explicit representation. In this section we describe (1) how the dynamics of an evolutionary system can be learned using a function approximator and, (2) how tools from machine learning and control theory can be used to guide a Darwinian population to a target state, as one example.

Referring to FIG. 3, a method 300 for learning and steering (e.g., controlling) evolutionary dynamics may include steps 1-16, according to some embodiments. Some embodiments of the steps of a method 300 for learning and steering evolutionary dynamics are described in further detail below.

Evolution as a Dynamical System

The evolution of a population can be expressed compactly as the mapping f: S×A→S which takes the state $s_t$ of a population at generation t and changes to the environment at generation t and produces the state $s_{t+1}$ of the population at the next generation.

Learning an Approximate Dynamics Model

In most cases, if not all, we do not have an explicit form of the evolutionary dynamics f of a population. In some cases however, it is possible to collect data from the real system and learn from it. Consider a population of algae growing in a bioreactor. In this system we can measure properties of the state such as chemical make-up of the water, photosynthetic activity, growth rate, etc. Furthermore, we can set and control other environmental parameters such as temperature, pH, light frequency, water flow-rate, etc. In this way we can collect a dataset of ($s_t$, $a_t$, $s_{t+1}$) tuples that implicitly define the true evolutionary dynamics of the population (see step 2 of method 300 in FIG. 3).

Using this data, we can, for example, train an approximator (e.g., linear regression, random forest, Gaussian process, neural network, deep neural network ("DNN"), matrix, non-parametric function, etc.) in a supervised setting to learn an approximate dynamics model $\hat{f}_\theta$ of the population's evolutionary dynamics f (see step 1 of method 300 in FIG. 3). The training of this approximator can be streamlined by pre-loading it with evolutionary models. Any suitable evolutionary model may be pre-loaded to the approximator, including (without limitation) the Price equation, Fisher's Fundamental Theorem, the Breeder's equation, the Wright/Fisher model, Hamilton's rule, etc. This approximate dynamics model can then be used to do optimal control of the system.

In the next sub-section, an embodiment of a technique suitable for optimal control of an evolutionary system is presented. This embodiment uses Model-Based Reinforcement Learning ("RL") to learn an approximator of the dynamics of the evolutionary system and uses the approximator to identify optimal controls for the system. However, in some embodiments, other suitable technique for utilizing dynamics in optimal control may be used. For example, a tabular approach may be used to learn the dynamics. In some embodiments, rather than learning the dynamics, the control process can operate on known, analytical functions. Also, optimal control techniques that are not model-based may be used. For example, rather than explicitly representing the dynamics, the controls can be identified using Model-Free Reinforcement Learning.

Control Using Model-Based Reinforcement Learning

When doing control, model-based reinforcement learning systems iterate between a planning phase (see steps 10-15 of method 300 in FIG. 3) and a learning phase (see steps 6-8 of method 300 in FIG. 3). In the planning phase, a learned policy (in the form of a neural network, or Gaussian Process, or Gaussian Mixture Model ("GMM"), etc.) is used to take actions in the system of interest (see step 12 of method 300 in FIG. 3) or a form of model-predictive control (MPC) is performed (see step 11 of method 300 in FIG. 3). For example, the approximate dynamics model $\hat{f}_\theta$ and a reward (or cost) function R(s, a) may be used to simulate trajectories for one or more time-steps T, and the first action $a_t$ of the trajectory which yields the highest reward R may be chosen (see step 11 of method 300 in FIG. 3). The action $a_t$ may be chosen using a learned policy, Model-Predictive Control ("MPC") (as in step 11 of method 300 in FIG. 3), or any other suitable technique. The chosen action may then be taken on the system of interest, and changes to the state of the system of interest may be observed (see step 12 of method 300 in FIG. 3). In this way, the model-based reinforcement learning system collects data $(s_t, a_t, s_{t+1})$ (see step 13 of method 300 in FIG. 3) which can then be used in the learning phase to further inform the approximate dynamics model $\hat{f}_\theta$.

Some embodiments of the optimal control techniques described herein can be used to optimally control any suitable systems of interest, including (without limitation) real-world evolutionary systems (e.g., biological systems), virtual Darwinian systems (e.g., Avida), memetic evolutionary systems in online environments, etc.

In some embodiments, the method 100 of FIG. 1 for learning and steering evolutionary dynamics may be implemented using the model-based reinforcement learning method of FIG. 3.

Evolutionarily Informed Learning

Naively learning evolutionary dynamics is possible but may be data- and computationally-intensive. This process can be accelerated by taking advantage of known features of evolutionary dynamics. For example, the model can be designed to include or otherwise account for evolutionary models of fixation rate, selection strength, the partition between change due to selection and the environment, behavior near evolutionary equilibria, etc.

In some embodiments, such evolutionary models are incorporated into the dynamics model $\hat{f}_\theta$, used to initialize or otherwise train the dynamics model $\hat{f}_\theta$, or otherwise used in method 300 to efficiently learn and control evolutionary dynamics.

Generality of Approach

An example of a method 300 for steering (e.g., controlling) the evolution of a population of organisms has been described. More generally, methods for steering the evolution of a population of entities (e.g., organisms) may include a two-phase approach to this problem. In a first stage, learned approximator(s) informed by data and evolutionary models may be used to learn evolutionary dynamics of the population of interest. In the second phase, optimal control techniques may be used to steer those dynamics to a new state.

Some embodiments are not limited to the above-described two-phase, model-based approach to steering the evolution of a population. Any suitable techniques for learning the evolutionary dynamics of a system of interest and/or taking action with respect to the system of interest (e.g., controlling inputs to the system of interest) based on the learned evolutionary dynamics may be used. In some embodiments, the actions taken with respect to the system of interest may change the direction or outcome of evolution within the system of interest, such than optimality criterion is met. In some embodiments, the dynamics of the system of interest are not learned explicitly, but instead learned implicitly through the process of taking actions, such as in the case of control using Model-Free Reinforcement Learning.

Exemplary System for Learning and Steering Evolutionary Dynamics

Figure 4:
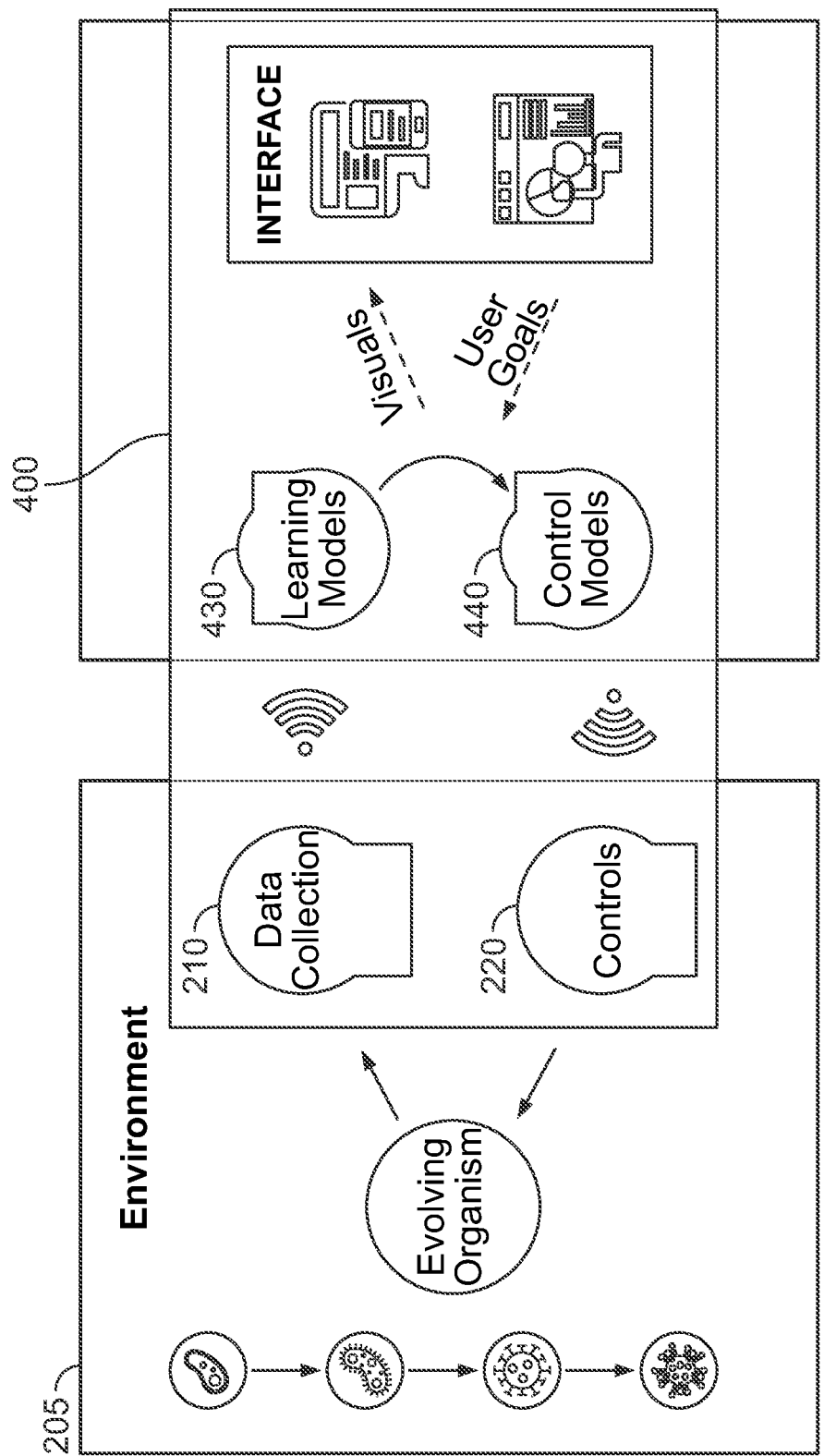
FIG. 4 depicts a block diagram of an example of a system for learning and steering evolutionary dynamics, according to some embodiments.

Referring to FIG. 4, a system 400 may perform the method 300 to learn and steer evolutionary dynamics of a population of entities (e.g., organisms) within an environment. In some embodiments, the system 400 is a closed-loop data-in controls-out system. In some embodiments, the system 400 includes one or more data collection modules 210, one or more control modules 220, one or more learning models 430, and one or more control models 440. Some embodiments of the components 210, 220, 430, 440 of the system 400 are described in further detail below.

The learning phase of the method 300 may be performed by any suitable system capable of collecting data on a population of organisms and environmental conditions. The control phase of the method 300 may be performed by any suitable system capable of performing the learning phase and also capable of controlling environmental parameters (e.g., in real time).

The data collection modules 210 may include one or more sensors (e.g. photodiodes, cameras, pH probes, thermometers, etc.) operable to collect data on the population (e.g. color, density, nutrient ratios, apoptosis rates, etc.) and/or the environment (e.g. temperature, brightness, humidity, etc.). Any suitable sensors may be used. The data collection modules may transfer the collected data to one or more processing devices, which may convert the data into a format compatible with the method 300.

The learning models 430 may model the evolutionary dynamics of the population within the environment 205. In some embodiments, the learning models 430 include one or more approximate dynamics models. Some examples of techniques for learning approximate dynamics models are described above. The system 400 may use such techniques during the learning phase of the method 300 to learn the approximate dynamics models.

The control models 440 may predict the changes in the dependent variables of the environment 205 that will result from taking an action $a_t$ with respect to the environment 205 (e.g., changing the values of one or more controllable environmental parameters) at a time t. In some embodiments, the control models 440 include one or more MPC models. The system 400 may use the control models 440 during the control phase of the method 300 to determine an action $a_t$ to be taken with respect to the environment 205. Some examples of techniques for determining an action (e.g., an optimal action) $a_t$ to be taken with respect to an environment 205 are described above. In some embodiments, after the action $a_t$ is selected, the control system 400 sends instructions to one or more of the control modules 220 to carry out the selected action by changing one or more controllable environmental parameters.

In some embodiments, the system 400 iteratively performs the learning phase and the control phase of the method 300 to reach a stable optimum with respect to the target goal and to maintain the environment's population at that optimum.

In some embodiments, a system 400 may have no control modules 220 (e.g., no available hardware to institute controls) suitable for performing a desired action $a_t$ during the control phase of the method 300. In such embodiments, the system 400 may report evolutionary predictions to aid the user in managing the system and making decisions.

In some embodiments, a user can use the method 300 and/or the system 400 to produce a desired end product (e.g. a bacteria that eats plastic), and then stop using the method 300 and/or system 400. In such embodiments, after the desired organism has been evolved, the user can proceed to synthesize its genome, or use any insights gained from the process for any suitable purpose.

Alternatively, the user may keep one or more organisms in the system 400, and may continue to perform the method 300. This might be the case, if, for example, the user's goal is to increase yields. By halting the method 300 or removing the organism from the system 400, the optimal yields would likely be lost over time. However, if kept in the system, the yields can be maintained against perturbations.

In some embodiments, the system 400 is operated in-house. For example, the "user" could be a provider or operator of the system 400. For example, the provider or operator of the system 400 could have the goal of evolving a yeast that produces heme for meat alternatives, and could perform the method 300 on in-house yeast reactors, and later sell its genome or other valuable product to other companies.

Some non-limiting examples of techniques for instituting controls with respect to taking actions to change an environment in order to steer evolution of entities within that environment have been described. Other aspects of the environment may or may not be held constant while such controls are being instituted. The system of controls may include subroutines to maintain one or more environmental parameters at fixed or approximately fixed values using MPC or other forms of controls including but not limited to PID (proportional-integral-derivative) and LQR (linear-quadratic regulator). These control routines may work in conjunction with or independently of the control methods and systems described above.

The technology described herein covers a wide range of organisms across the tree of life. The possible systems in which some embodiments can be used may range from all-in-one data collection and environmental control units, such as bioreactors, to distributed nets of disconnected sensors, data collection hardware, and manual inputs. The possible goals some embodiments can achieve may range from creating a new type of organism, to keeping a population at some maximum value, to a time-varying, multi-factorial goal that runs continuously.

Some Examples of Use Cases

Below we present some non-limiting examples of use cases, which represent only a small sample of the applications of the techniques described herein.

Maximizing Algal Yields in a Photobioreactor

Figure 5:
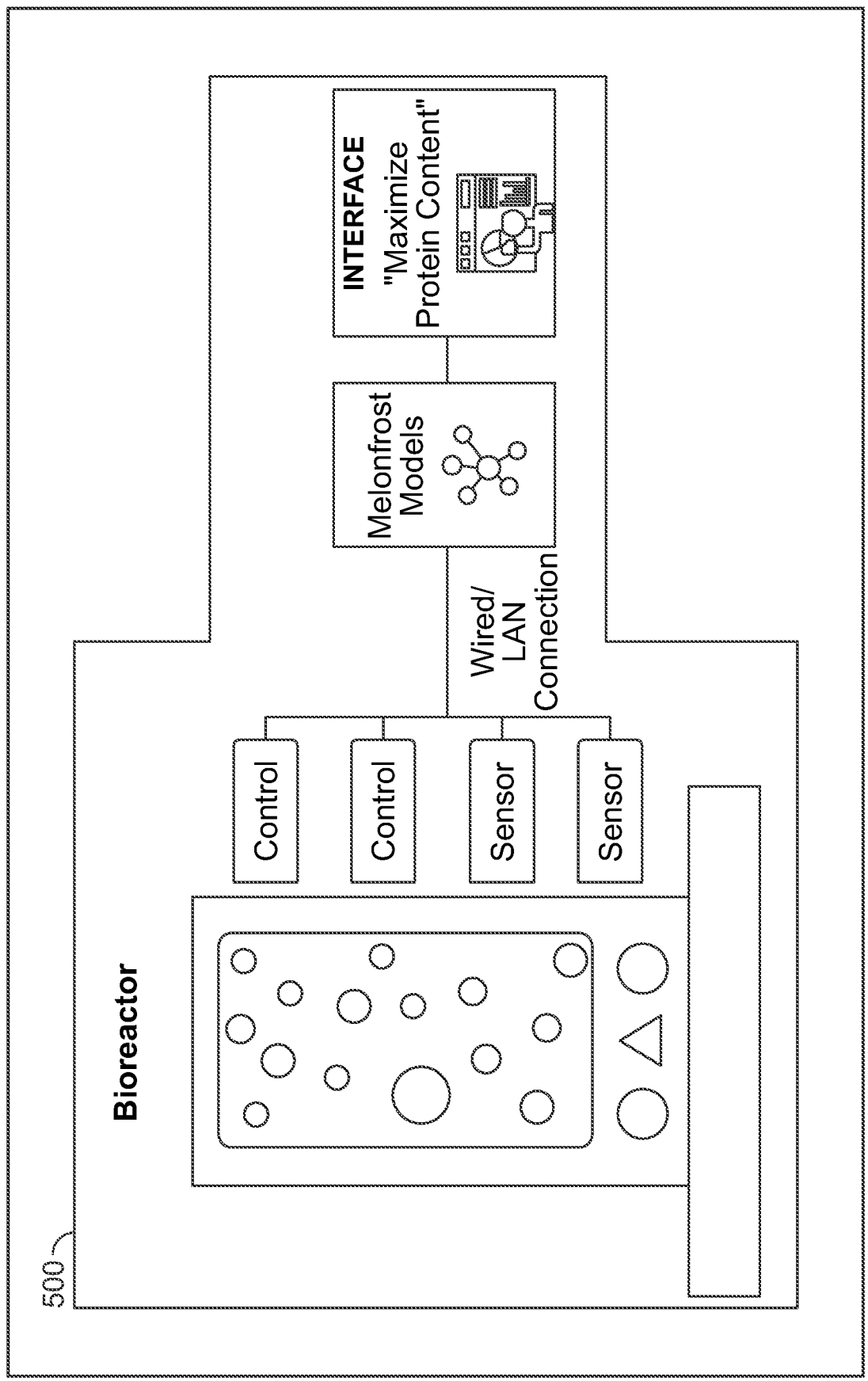
FIG. 5 depicts a block diagram of a system for learning and steering evolutionary dynamics applied to a bioreactor system, according to some embodiments.

Referring to FIG. 5, an embodiment of a system 500 for learning and steering evolutionary dynamics may be applied to a bioreactor system. A producer of algae (for edible protein, biofuel, textiles) may use industrial photobioreactors to cultivate single-celled organisms. In some embodiments, the system 500, e.g., algal yields in the photobioreactor, can include one or more of the following environmental attributes: temperature, pH, mixing speed, flow rate, ratio of carbon dioxide to oxygen, and/or gas bubbling rate as measured from within the photobioreactor. In some embodiments, the system 500, e.g., algal yields in the photobioreactor, can include one or more characteristics such as: population and/or the environmental temperature, pH, mixing speed, ratio of carbon dioxide to oxygen, and/or gas bubbling rate, optical density, and/or an protein content. In some embodiments, the system 500, e.g., algal yields in a photobioreactor, can include one or more optimality metrics such as: a level of protein content within the algae cultivated in a bioreactor, among others. In some embodiments, the system 500 is an embodiment the system 200 of FIG. 2 and/or the system 400 of FIG. 4. In an example, the systems 200/400 can encompass the system 500, therefore the description for each of the systems 200/400 also apply to the system 500. The producer may wish to increase the protein content of harvested algae. The bioreactor may have in-built sensors for collecting data on the environment within the bioreactor and the organisms in the bioreactor, e.g., temperature, pH, mixing speed, carbon dioxide ($CO_2$) to oxygen ($O_2$) ratio, gas bubbling rate, optical density, a proxy for protein content, etc. The bioreactor also may have automatically programmable controls which can adjust environmental conditions within the bioreactor (e.g., temperature, pH, mixing speed, carbon dioxide ($CO_2$) to oxygen ($O_2$) ratio, gas bubbling rate, etc.).

In some embodiments, the learning and control system 500 interfaces directly with the in-built software of the reactors. The user may select the goal of maximizing protein content, and the system may run uninterrupted. A user interface may display algal yields, and a confidence interval suggesting how close the protein content is to maximal protein content. The goal may have other components, such as "maximize protein content per dollar input."

Using the above-described techniques, the system 500 may learn the evolutionary dynamics of the algae within the bioreactor system and control the environmental conditions within the bioreactor to achieve an optimality criterion (e.g., a level of protein content within the cultivated algae that matches or exceeds a desired threshold level.)

Maximizing Efficacy of an Oncolytic Virus

Figure 6:
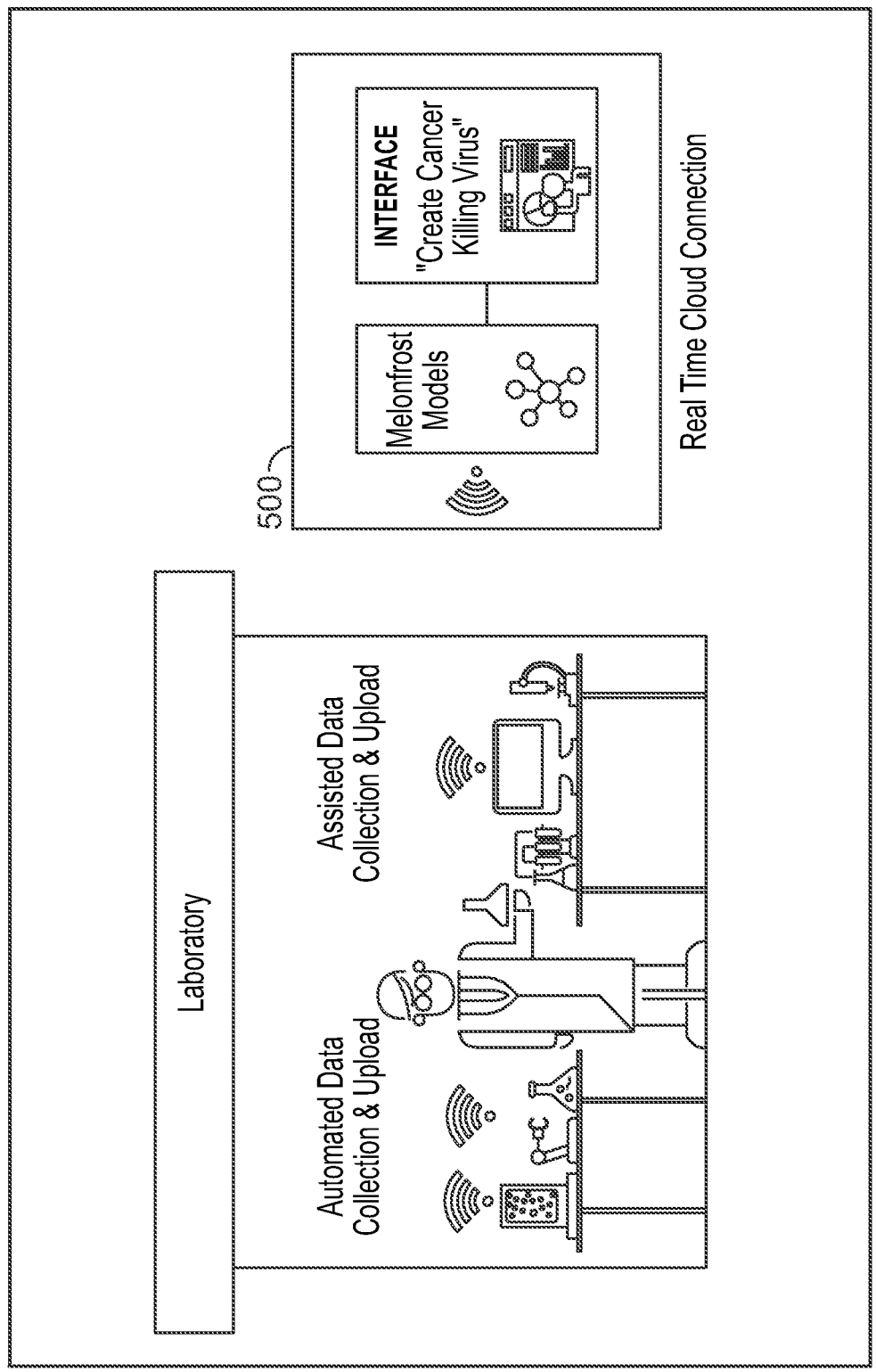
FIG. 6 depicts a block diagram of a system for learning and steering evolutionary dynamics applied to a laboratory environment, according to some embodiments.

Referring to FIG. 6, an embodiment of a system 500 for learning and steering evolutionary dynamics may be applied to a laboratory environment. A medical technology company may cultivate viruses and human cell lines in the lab, with the goal of identifying oncolytic viruses which target cancer cells without causing excessive damage to normal cells. The company may collect real-time data on drug cocktails, growth media contents, viral load of cells, cell waste products, and semi-real time data on the genetics of the viruses. Some of this data may be automatically uploaded to the system 500, and other data may be manually entered by the user. The user may specify the goal of increasing oncolytic efficacy, and manually run experiments until the desired efficacy is achieved. Using the above-described techniques, the system 500 may learn the evolutionary dynamics of the oncolytic viruses within the growth media and control the environmental conditions of the growth media to achieve an optimality criterion (e.g., a level of oncolytic efficacy that matches or exceeds a threshold level, as well as a level of damage to normal cells that matches or falls below a threshold level). In some embodiments, as applied to the laboratory environment (e.g., as described above), the system 500 can include one or more attributes: one or more contents of the growth medium (e.g. cancer cell genotype markers, measured through sequencing) and/or one or more contents of the drug candidates (e.g. oncolytic viral genotype from a library). In some embodiments, the characteristics of the population within the laboratory environment, the system 500, can include the contents of the growth medium (measured as input variable by cancer cell genotype), the contents of the drug candidates (viral genotypes taken from known library), a viral load of the growth medium (measured, e.g. through PCR analysis), one or more genetic characteristics of the virus (e.g. known genetic markers), and/or one or more cell waste products in the test wells (e.g. fluorescence spectroscopy measuring quantity of known cell waste amino acid). In some embodiments, the laboratory environment, e.g., the system 500, can include one or more optimality metrics such as: a level of oncolytic efficacy of the virus.

Maximizing Albumin Output of E-coli

Figure 7:
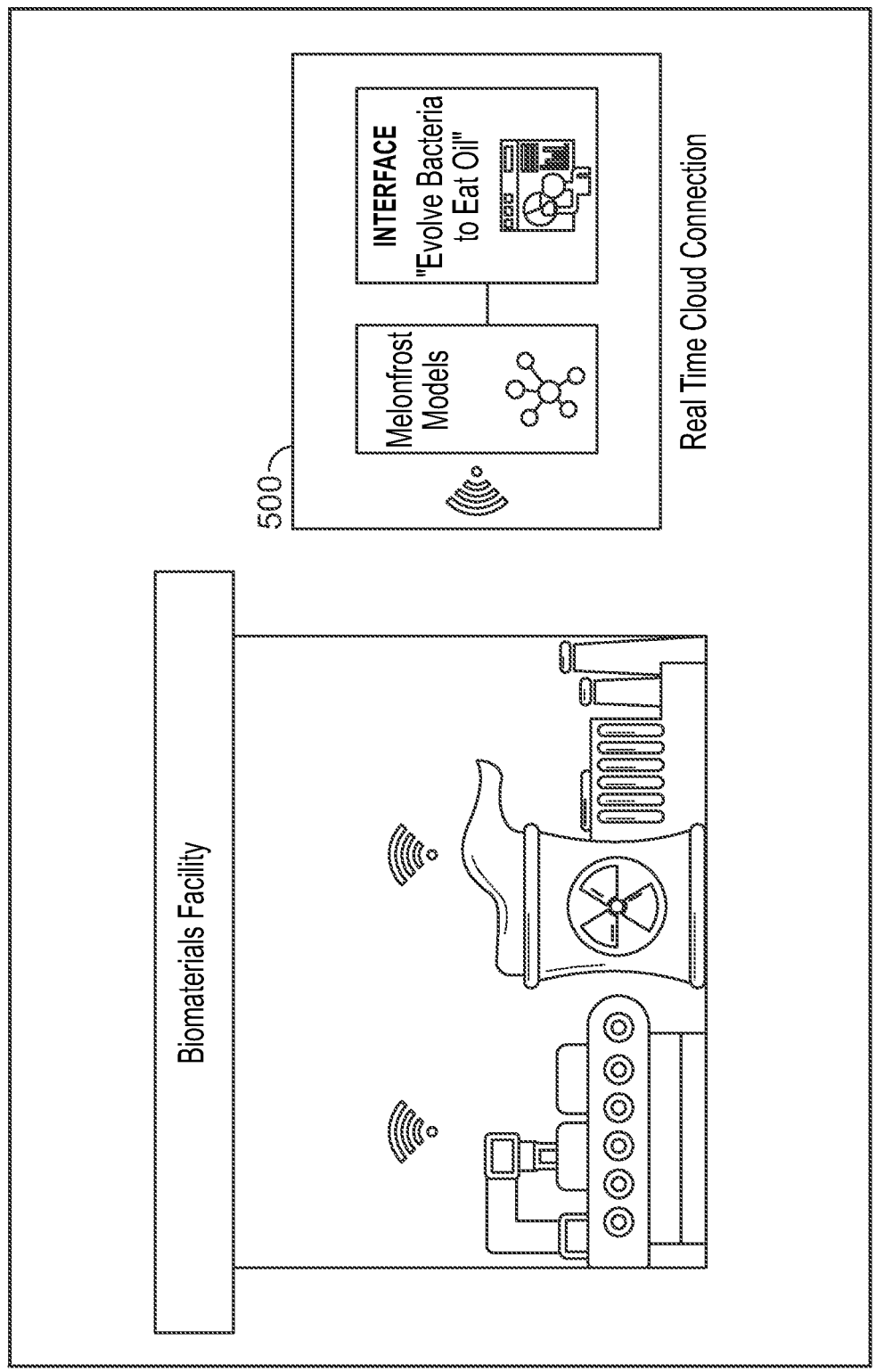
FIG. 7 depicts a block diagram of a system for learning and steering evolutionary dynamics applied to a biomaterials production facility, according to some embodiments.

Referring to FIG. 7, an embodiment of a system 500 for learning and steering evolutionary dynamics may be applied to a biomaterials production facility. A biomaterials company may mass produce albumin for use in hospitals. The company may grow *Escherichia coli* ("*E. coli*") which have been genetically modified to produce human albumin protein in specialized reactors which automatically harvest albumin, and which automatically gather data on a suite of bacterial characteristics (e.g., cell size, cell death, optical density, waste products, albumin output, etc.) and environmental characteristics (e.g. temperature, growth media, mixing, gas input, pressure, environmental structure, etc.).

The company's goal may be to maximize albumin output. The interface of the system 500 may alert the user when the system's confidence that maximal albumin outputs have been achieved is above a pre-defined (e.g., user-specified) threshold level. Similar goals may include generating a microbe that efficiently consumes oil, or secretes plastic, etc.

Using the above-described techniques, the system 500 may learn the evolutionary dynamics of the *E. coli* within the reactors and control the environmental conditions within the reactors to achieve an optimality criterion (e.g., a level of albumin output from the *E. coli* that matches or exceeds a desired threshold level.)

In some embodiments, as applied to a biomaterials production facility (e.g., as described above), the system 500 can include one or more of the following environmental attributes: a temperature within a bioreactor (e.g., bioreactor), one or more contents of a growth medium within the bioreactor (e.g. substrate composition as input, or spectroscopic analysis of sugars), a mixing rate, flow rate, a gas input to the reactor, a pressure within the bioreactor, and/or an environmental structure within the bioreactor. In some embodiments, as applied to a biomaterials production facility, the system 500 can include one or more of the following characteristics: a cell size of albumin protein within the reactor, a rate of cell death within the reactor, an optical density within the reactor, levels of one or more waste products within the reactor, and/or level of albumin output within the reactor (e.g. through MIR spectroscopy or a targeted biosensor). In some embodiments, as applied to a biomaterials production facility, the system 500 can include one or more an optimality metric such as albumin output.

Maximizing Yields of Indoor Farmed Greens

Figure 8:
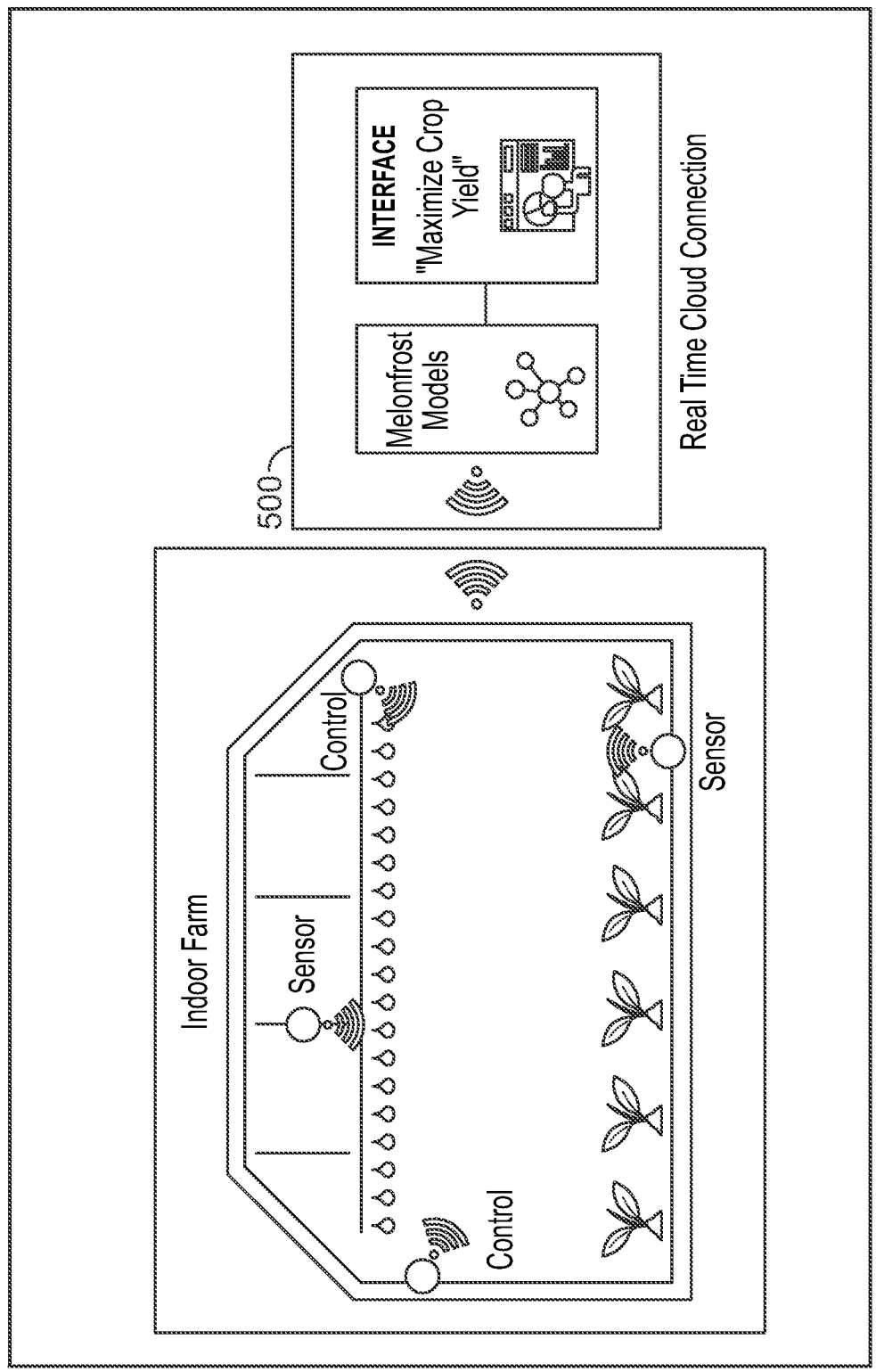
FIG. 8 depicts a block diagram of a system for learning and steering evolutionary dynamics applied to an indoor farming environment, according to some embodiments.

Referring to FIG. 8, an embodiment of a system 500 for learning and steering evolutionary dynamics may be applied to an indoor farming environment. An indoor farming company may have a closed loop seed to harvest vertical farming facility, equipped with robotic harvesters, computer vision technology, and an automatically controllable environment. The company's goal may be to maximize yield of greens (e.g., in pounds) per dollar, without sacrificing quantity or nutritional quality of harvest. The user interface of the system 500 may output a visual display (e.g., a continuous visual display) of yield per dollar, and its predicted trajectory. The user may keep the system 500 running continuously, as the system 500 may maintain the population at optimality as long as the system remains active. The user can be agnostic to whether the goal is achieved, for example, by reducing time to harvest or increasing yield per square foot, or can specify a preference. The indoor farming environment may have automatically programmable controls which can adjust environmental conditions within the environment (e.g., temperature, light levels, application of water, soil treatments, soil moisture content, etc.). In some embodiments, the structure of the crop population within the farming facility (e.g., rotation of greens, density of cultivation, etc.) may also be controlled.

Using the above-described techniques, the system 500 may learn the evolutionary dynamics of the crop within the farming environment and control the environmental conditions within the farming environment to achieve an optimality criterion (e.g., a level of crop yield per square foot that matches or exceeds a desired threshold level.)

Predicting Long Term Trends in Outdoor Aquaculture

Figure 9:
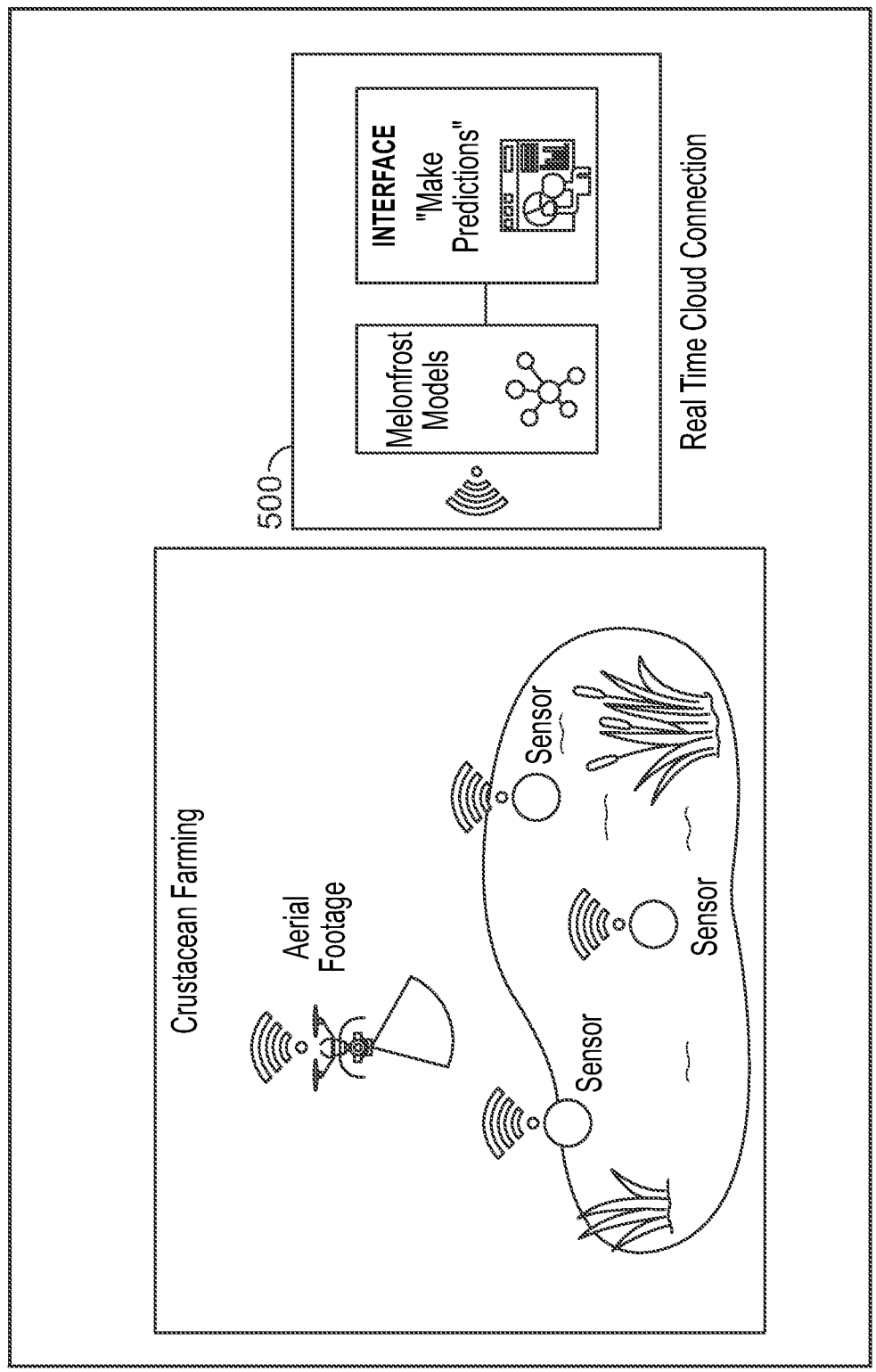
FIG. 9 depicts a block diagram of a system for learning and steering evolutionary dynamics applied to an aquaculture environment, according to some embodiments.

Referring to FIG. 9, an embodiment of a system 500 for learning and steering evolutionary dynamics may be applied to an aquaculture environment. An outdoor aquaculture producer may want to better manage an aquaculture operation. The operation may have a wide range of data collection tools, including sensors in the water, satellite imagery, drones, measuring things like water temperature, salinity, population structure, turbidity, feeding rate, etc. However, the producer may have limited ability to automatically control the environment. The producer may wish to better manage nutrient levels and care cycles, and to prepare for evolutionary changes in production, with a goal of maximizing harvest, in weight, per dollar. The producer may connect the aquaculture operation's data streams to the system 500, and the user interface of the system 500 may provide running predictions about various features of the population, as well as learned relationships between certain environmental parameters and the population.

Cell Morphology

A biomaterials company may use a microbial organism to produce a material e.g. for the textile or construction industry. The cell morphology of the organism may contribute significantly to the relevant properties of the final product, such as tensile strength, durability, flexibility, etc. The company may cultivate this organism in some form of liquid culture, such as a bioreactor or fermentation tank. Data are automatically gathered on various properties of the environment, bioprocess conditions, and the organism itself. One of these parameters may be a measurement, either directly, or by proxy, of the organism's cell morphology, e.g. using cameras and computer vision tools. Other parameters which may be measured (and which may affect the evolution of the relevant phenotype) may include mixing speed, shear force, temperature, pH, nutrient density, or substrate composition The company's goal may be to modify the cell morphology of the organism to improve the characteristics of the final product. For example, their goal may be to maximize the density of microbial mats or filaments, increase the elongation of cells, or decrease clumping of cells at low stir speeds. The interface of system 500 may alert the user when the morphology has reached some predefined goal (e.g., a minimum cell wall thickness, a maximum density of filaments, or a specific geometry of a cell matrix).

Using the above-described techniques, the system 500 may learn the evolutionary dynamics of the microbial organism within the reactors or fermentation tanks and control the environmental conditions within the reactors or fermentation tanks to achieve an optimality criterion (e.g., a match, within bounds, to a pre-set cell or cell matrix geometry.)

Secretion

A therapeutics company may have engineered a microbial organism to produce a valuable therapeutic (e.g., drug) that would otherwise have to be synthesized, or harvested from plants or animals in an expensive manner. Therapeutics could include psychoactive compounds, monoclonal antibodies, antibiotics, etc. The microbial organism may successfully produce the drug, but may not successfully secrete it from its cells. The drug may then be difficult to extract, or may be destroyed inside the cells themselves. The organism may be cultivated in a bioreactor, and data are automatically gathered on various properties of the environment, bioprocess conditions, and the organism itself. One of these parameters may be a measurement of the concentration of the drug in solution. Other parameters may include mixing speed, shear force, temperature, pH, nutrient density, substrate composition, or antibiotic addition rate.

The company's goal may be to increase the secretion of the drug. The interface of system 500 may alert the user when concentration in the solution has reached some predefined goal.

Using the above-described techniques, the system 500 may learn the evolutionary dynamics of the microbial organism within the and control the environmental conditions within the reactors to achieve an optimality criterion (e.g., concentration of the drug in solution).

Pandemic Evolution

A governmental entity may wish to determine interventions to prevent or limit the spread of a viral contagion among a population. They may have access to paired data matching viral genotypes to patient phenotypes. The genotypes of the viruses may be partial, and the phenotypes may include information on patients' DNA, immune system, or other relevant traits. They may also have information on intervention methods, such as lock-downs, migration restrictions, vaccinations, or antiviral treatments. They may also have measurements of the virus's replication rate in the population, such as an estimate of Ro.

The entity's goal may be to develop more effective interventions to limit the spread of the virus. The entity may connect the data stream on viruses and patients to the system 500, and the user interface of the system 500 may provide predictions about the relationship between patient phenotypes and/or genotypes and the virus, as well as suggestions for effective interventions to limit the spread of the virus.

Further Use Cases

Some non-limiting examples of applications of some embodiments have been described. Some embodiments of the systems and methods described herein may be applied across agriculture, aquaculture, bioengineering, synthetic biology, biomaterials, medicine, pharmaceuticals, biofuels, and any industry or system that uses biological organisms. The techniques described herein may be used to address any biological goal or challenge for which the target change to the organism or population of organisms can be measured directly or indirectly, including but not limiting to increasing yields, decreasing virulence or contagiousness, increase strength of a biomaterial, changing any measurable attribute of a biomaterial, making an organism produce a new waste material (e.g. plastic, gold), making an organism break down a new material (e.g. oil, plastic), changing the flavor or scent of an edible organism, making an organism less competitive, making an organism produce a more efficient biofuel, making an organism consume less water, nutrients, or fertilizer, changing the measurable (e.g. through fluorescence) conformation of a protein produced by an organism, changing an organism's tolerance of certain conditions, such as higher temperature or lower pH, changing the expression levels of a protein, changing the genetic architecture of a gene network, or controlling the spread of a meme (e.g., an ad) in a virtual environment (e.g., the internet), etc.

Further Description of Some Embodiments

In some examples, some or all of the processing described above can be carried out on a personal computing device, on one or more centralized computing devices, or via cloud-based processing by one or more servers. In some examples, some types of processing occur on one device and other types of processing occur on another device. In some examples, some or all of the data described above can be stored on a personal computing device, in data storage hosted on one or more centralized computing devices, or via cloud-based storage. In some examples, some data are stored in one location and other data are stored in another location. In some examples, quantum computing can be used. In some examples, functional programming languages can be used. In some examples, electrical memory, such as flash-based memory, can be used.

Figure 10:
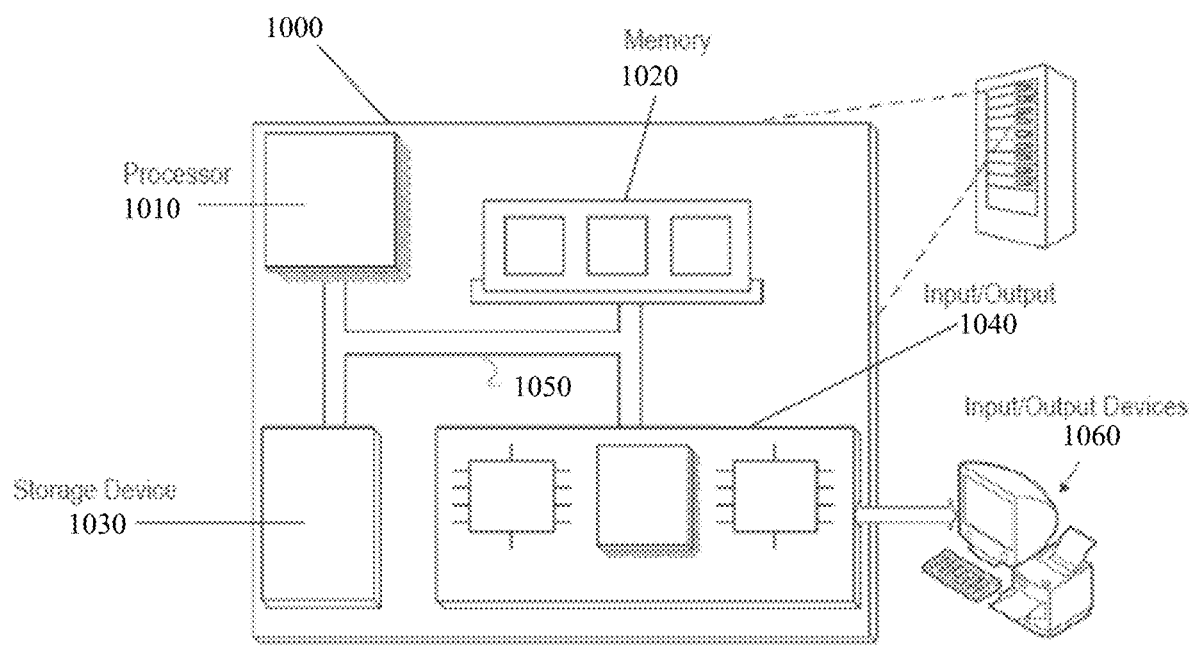
FIG. 10 depicts a diagram of an example computer system that may be used in implementing some embodiments of the systems and methods described herein.

FIG. 10 is a block diagram of an example computer system 1000 that may be used in implementing the technology described in this document. General-purpose computers, network appliances, mobile devices, or other electronic systems may also include at least portions of the system 1000. The system 1000 includes a processor 1010, a memory 1020, a storage device 1030, and an input/output device 1040. Each of the components 1010, 1020, 1030, and 1040 may be interconnected, for example, using a system bus 1050. The processor 1010 is capable of processing instructions for execution within the system 1000. In some implementations, the processor 1010 is a single-threaded processor. In some implementations, the processor 1010 is a multi-threaded processor. The processor 1010 is capable of processing instructions stored in the memory 1020 or on the storage device 1030.

The memory 1020 stores information within the system 1000. In some implementations, the memory 1020 is a non-transitory computer-readable medium. In some implementations, the memory 1020 is a volatile memory unit. In some implementations, the memory 1020 is a nonvolatile memory unit.

The storage device 1030 is capable of providing mass storage for the system 1000. In some implementations, the storage device 1030 is a non-transitory computer-readable medium. In various different implementations, the storage device 1030 may include, for example, a hard disk device, an optical disk device, a solid-date drive, a flash drive, or some other large capacity storage device. For example, the storage device may store long-term data (e.g., database data, file system data, etc.). The input/output device 1040 provides input/output operations for the system 1000. In some implementations, the input/output device 1040 may include one or more of a network interface devices, e.g., an Ethernet card, a serial communication device, e.g., an RS-232 port, and/or a wireless interface device, e.g., an 802.11 card, a 3G wireless modem, or a 4G wireless modem. In some implementations, the input/output device may include driver devices configured to receive input data and send output data to other input/output devices, e.g., keyboard, printer and display devices 1060. In some examples, mobile computing devices, mobile communication devices, and other devices may be used.

In some implementations, at least a portion of the approaches described above may be realized by instructions that upon execution cause one or more processing devices to carry out the processes and functions described above. Such instructions may include, for example, interpreted instructions such as script instructions, or executable code, or other instructions stored in a non-transitory computer readable medium. The storage device 1030 may be implemented in a distributed way over a network, such as a server farm or a set of widely distributed servers, or may be implemented in a single computing device.

Although an example processing system has been described in FIG. 10, embodiments of the subject matter, functional operations and processes described in this specification can be implemented in other types of digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "system" may encompass all kinds of apparatus, devices, and machines for processing data, including by way of example a programmable processor, a computer, or multiple processors or computers. A processing system may include special purpose logic circuitry, e.g., an FPGA (field programmable gate array) or an ASIC (application specific integrated circuit). A processing system may include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, an engine, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program can include, by way of example, general or special purpose microprocessors or both, or any other kind of central processing unit. Generally, a central processing unit will receive instructions and data from a read-only memory or a random access memory or both. A computer generally includes a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps or stages may be provided, or steps or stages may be eliminated, from the described processes. Accordingly, other implementations are within the scope of the following claims.

Terminology

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

What is claimed is:

1. A computer-implemented method for control of organism evolution through environmental modification, the method comprising:
    initializing a bioreactor, a well of the initialized bioreactor comprising a population of evolving organisms;
    determining a set of selection pressures affecting one or more characteristics of the population of evolving organisms;
    (a) applying the set of selection pressures to the population;
    (b) determining, with one or more sensor devices, a state of the population and storing, with one or more processing devices, the determined population state in a population dataset;
    (c) detecting, with the one or more processing devices, whether the population has reached an evolutionarily stable state in response to the applying of the set of selection pressures by determining a stationarity of the state of the population of evolving organisms;
    (d) responsive to detecting that the population has reached the evolutionarily stable state:
        obtaining stable state data representing the evolutionarily stable state,
        redetermining, with the one or more processing devices, the set of selection pressures based on a selection pressure policy, wherein redetermining the set of selection pressures comprises changing the set of selection pressures at least in part, and
        storing the stable state data and the redetermined set of selection pressures in a stable state dataset;
    (e) determining, with the one or more processing devices, whether one or more stopping criteria have been met; and
    repeating steps (a)-(e) until at least one of the stopping criteria is met,
    wherein in repeating steps (a) and (c), the set of selection pressures comprise the set of selection pressures redetermined in a previous iteration of step (d), and wherein an evolutionarily stable state is a particular state to which the population of evolving organisms tends to return following perturbation from that particular state.

2. The method of claim 1, wherein determining the set of selection pressures comprises randomly determining the set of selection pressures.

3. The method of claim 1, wherein determining the population state comprises determining a morphology of the organisms in the population.

4. The method of claim 1, wherein determining the population state comprises measuring at least one of: a yield of the population, a virulence of the population, a contagiousness of the population, a strength of a biomaterial produced by the population, a change in a measurable attribute of a biomaterial, a waste material production level of the population, an efficiency with which the population breaks down a material, a flavor or scent of an edible organism of the population, a competitive behavior of the population, an efficiency with which the population produce fuels, a water consumption level of the population, a nutrient consumption of the population, or fertilizer consumption of the population.

5. The method of claim 1, wherein detecting whether the population state has reached an evolutionarily stable state comprises performing a time series analysis on the population dataset.

6. The method of claim 5, wherein performing a time series analysis on the population dataset comprises:
    fitting a first degree polynomial to a leading window of a time series of population states in the population dataset;
    applying an autocorrelation function (ACF) to the leading window of the time series of population states; and/or
    fitting a regression model to the time series of population states and testing a null hypothesis that a unit root is present in the regression model.

7. The method of claim 1, wherein determining the selection pressures comprises applying at least one of a reinforcement learning policy or an optimization-based policy.

8. A system for control of organism evolution through environmental modification, the system comprising:
    a bioreactor operable to perform one or more actions affecting one or more attributes of an environment of a well of the bioreactor, the well of bioreactor including a population of evolving organisms;
    one or more sensor devices operable to collect data indicating one or more characteristics of the population and/or attributes of the environment; and
    one or more computers and one or more storage devices storing instructions operable, when executed by the computers, to cause the computers to perform operations including:
        initializing the bioreactor, the well of the initialized bioreactor comprising the population of evolving organisms;
        determining a set of selection pressures affecting one or more characteristics of the population of evolving organisms;
        (a) applying the set of selection pressures to the population;
        (b) determining, with the one or more sensor devices, a state of the population and storing the determined population state in a population dataset;
        (c) detecting whether the population has reached an evolutionarily stable state in response to the applying of the set of selection pressures by determining a stationarity of the state of the population of evolving organisms;
        (d) responsive to detecting that the population has reached the evolutionarily stable state:
            obtaining stable state data representing the evolutionarily stable state, redetermining the set of selection pressures based on a selection pressure policy, wherein redetermining the set of selection pressures comprises changing the set of selection pressures at least in part, and storing the stable state data and the redetermined set of selection pressures in a stable state dataset;

(e) determining whether one or more stopping criteria have been met; and repeating steps (a)-(e) until at least one of the stopping criteria is met, wherein in repeating steps (a) and (c), the set of selection pressures comprise the set of selection pressures redetermined in a previous iteration of step (d), and wherein an evolutionarily stable state is a particular state to which the population of evolving organisms tends to return following perturbation from that particular state.

9. The system of claim 8, wherein determining the set of selection pressures comprises randomly determining the set of selection pressures.

10. The system of claim 8, wherein determining the population state comprises determining a morphology of the organisms in the population.

11. The system of claim 8, wherein determining the population state comprises measuring at least one of: a yield of the population, a virulence of the population, a contagiousness of the population, a strength of a biomaterial produced by the population, a change in a measurable attribute of a biomaterial, a waste material production level of the population, an efficiency with which the population breaks down a material, a flavor or scent of an edible organism of the population, a competitive behavior of the population, an efficiency with which the population produce fuels, a water consumption level of the population, a nutrient consumption of the population, or fertilizer consumption of the population.

12. The system of claim 8, wherein detecting whether the population state has reached an evolutionarily stable state comprises performing a time series analysis on the population dataset.

13. The system of claim 12, wherein performing a time series analysis on the population dataset comprises:

fitting a first degree polynomial to a leading window of a time series of population states in the population dataset;

applying an autocorrelation function (ACF) to the leading window of the time series of population states; and/or fitting a regression model to the time series of population states and testing a null hypothesis that a unit root is present in the regression model.

14. The system of claim 8, wherein determining the selection pressures comprises applying at least one of a reinforcement learning policy or an optimization-based policy.

15. A system for control of organism evolution through environmental modification, the system comprising:

a bioreactor operable to perform one or more actions affecting one or more attributes of an environment of a well of the bioreactor, the well of the bioreactor including a population of evolving organisms;

one or more sensor devices operable to collect data indicating one or more characteristics of the population and/or attributes of the environment; and one or more computers and one or more storage devices storing instructions operable, when executed by the computers, to cause the computers to perform operations including:

identifying an optimality metric, wherein a value of the optimality metric depends on at least one of the characteristics of the population, and wherein the value of the optimality metric does not satisfy an optimality criterion at an initial time t, determining a set of selection pressures affecting one or more characteristics of the population of evolving organisms, (a) controlling the bioreactor to apply the set of selection pressures to the population by performing one or more of the actions, (b) controlling at least one of the sensor devices to collect data indicating a value of at least one of the characteristics of the population, (c) detecting whether the population has reached an evolutionarily stable state in response to the controlling of the bioreactor to apply the set of selection pressures by determining a stationarity of a state of the population of evolving organisms, (d) responsive to detecting that the population has reached the evolutionarily stable state, redetermining the set of selection pressures based on a selection pressure policy, wherein redetermining the set of selection pressures comprises changing the set of selection pressures at least in part, and repeating steps (a)-(d) until a stopping criterion is met, wherein, in repeating steps (a) and (c), the set of selection pressures comprise the set of selection pressures redetermined in a previous iteration of step (d), wherein an evolutionarily stable state is a particular state to which the population of evolving organisms tends to return following perturbation from that particular state, and wherein the stopping criterion is met when (1) a number of iterations of steps (a)-(d) reaches or exceeds a maximum number of iterations, or (2) the collected data indicate that the value of the optimality metric satisfies an optimality criterion.

16. The system of claim 15, wherein:

the bioreactor is a photobioreactor;

the population of evolving organisms comprises a plurality of single-celled organisms;

the attributes of the environment include temperature, pH, mixing speed, ratio of carbon dioxide to oxygen, and/or gas bubbling rate;

the characteristics of the population include optical density, and/or an indicator of protein content;

the optimality metric comprises a level of protein content within algae cultivated in the bioreactor; and the optimality criterion is satisfied when the value of the optimality metric meets or exceeds a threshold value.

17. The system of claim 15, wherein:

the well of the bioreactor comprises a growth medium in which an oncolytic virus is cultivated and the bioreactor further comprises one or more test wells, each test well including viable cancer cells and a drug candidate comprising the oncolytic virus;

the population of evolving organisms comprises the oncolytic virus;

the attributes of the environment include one or more contents of the growth medium and/or one or more contents of the drug candidates;

the characteristics of the population include a viral load of the growth medium, one or more genetic characteristics of the oncolytic virus, and/or one or more cell waste products in the test wells;

the optimality metric comprises a level of oncolytic efficacy of the oncolytic virus; and the optimality criterion is satisfied when the level of oncolytic efficacy of the oncolytic virus meets or exceeds a threshold value.

18. The system of claim 15, wherein:

the bioreactor is a biomaterial production reactor;

the population of evolving organisms comprises *Escherichia coli* ("*E. coli*") genetically modified to produce human albumin protein;

the attributes of the environment include a temperature within the reactor, one or more contents of a growth medium within the reactor, a mixing rate within the reactor, a gas input to the reactor, a pressure within the reactor, and/or an environmental structure within the reactor;

the characteristics of the population include a cell size of albumin protein within the reactor, a rate of cell death within the reactor, an optical density within the reactor, levels of one or more waste products within the reactor, and/or level of albumin output within the reactor;

the optimality metric comprises the level of albumin output; and the optimality criterion is satisfied when the level of albumin output of the *E. coli* meets or exceeds a threshold value.

19. The system of claim 15, wherein step (c) further includes training an approximate model of an evolutionary dynamics of the evolving organisms based, at least in part, on the action(s) previously performed and the data previously collected.

20. The system of claim 19, wherein in each iteration of step (a), the at least one action is selected based, at least in part, on an output of a model-predictive control (MPC) process performed using the approximate model.

* * * * *